United States Patent
Jenkins et al.

(10) Patent No.: US 12,187,781 B2
(45) Date of Patent: Jan. 7, 2025

(54) CO-RECEPTOR AFFINITY ENHANCED MAJOR HISTOCOMPATIBILITY CLASS II MOLECULES

(71) Applicant: Regents of the University of Minnesota, Minneapolis, MN (US)

(72) Inventors: Marc Kevin Jenkins, Minneapolis, MN (US); Thamotharampillai Dileepan, Minneapolis, MN (US); Deepali Malhotra, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 985 days.

(21) Appl. No.: 17/264,707

(22) PCT Filed: Aug. 1, 2019

(86) PCT No.: PCT/US2019/044605
§ 371 (c)(1),
(2) Date: Jan. 29, 2021

(87) PCT Pub. No.: WO2020/028627
PCT Pub. Date: Feb. 6, 2020

(65) Prior Publication Data
US 2021/0300989 A1 Sep. 30, 2021

Related U.S. Application Data

(60) Provisional application No. 62/713,388, filed on Aug. 1, 2018.

(51) Int. Cl.
*G01N 33/50* (2006.01)
*C07K 14/74* (2006.01)
*G01N 33/543* (2006.01)
*G01N 33/58* (2006.01)

(52) U.S. Cl.
CPC ..... *C07K 14/70539* (2013.01); *G01N 33/505* (2013.01); *G01N 33/54366* (2013.01); *G01N 33/582* (2013.01); *C07K 2319/00* (2013.01)

(58) Field of Classification Search
CPC .......... C07K 14/70539; C07K 2319/00; G01N 33/505; G01N 33/54366; G01N 33/582
See application file for complete search history.

(56) References Cited

U.S. PATENT DOCUMENTS

2002/0115157 A1 8/2002 Davis et al.

OTHER PUBLICATIONS

Colman et al in Research in Immunology (145(1):33-36, 1994) (Year: 1994).*
Abaza et al in Journal of Protein Chemistry (11(5):433-444, 1992) (Year: 1992).*
Lederman et al in Molecular Immunology (28:1171-1181, 1991 (Year: 1991).*
Altman et al., (1996). "Phenotypic analysis of antigen-specific T lymphocytes," Science, 274:94-96.
Altschul et al., (1990). "Basic local alignment search tool," J. Mol. Biol., 215:403-410.
Altschul et al., (1997). "Gapped BLAST and PSI-BLAST: a new generation of protein database search programs," Nucleic Acids Res., 25:3389-3402.
Beckett et al., (1999). "A minimal peptide substrate in biotin holoenzyme synthetase-catalyzed biotinylation," Protein Sci., 8:921-929.
BioLegend. "Mouse Alloantigens," available online at <https://www.biolegend.com/Files/Images/media_assets/support_resource/BL_MouseAlloantigens_041116.pdf>, retrieved on Jul. 2024, 3 pages.
Bloom et al., (2009). "In the light of directed evolution: Pathways of adaptive protein evolution," Proc. Natl. Acad. Sci. USA, 106(Suppl1):9995-10000.
Bunch et al., (1988). "Characterization and use of the *Drosophila* metallothionein promoter in cultured *Drosophila melanogaster* cells," Nucl. Acids Res., 16:1043-1061.
Cibrian et al., (2017). "CD69: from activation marker to metabolic gatekeeper," Eur. J. Immunol., 47:946-953.
Corr et al., (1994). "T cell receptor-MHC class I peptide interactions: affinity, kinetics, and specificity," Science, 265:946-949.
Crawford et al., (1998). "Detection of antigen-specific T cells with multivalent soluble class II MHC covalent peptide complexes," Immunity, 8:675-682.
Davis et al., (2003). "The nature of molecular recognition by T cells," Nat. Immunol., 4:217-224.
Dileepan et al., (2015). "In Situ Peptide-MHC-II Tetramer Staining of Antigen-Specific CD4+ T Cells in Tissues," PLoS ONE, 10(6):e0128862, 10 pages.
Dileepan et al., (2021). "MHC class II tetramers engineered for enhanced binding to CD4 improve detection of antigen-specific T cells," Nature Biotechnology, 39:943-948.
Doherty et al., (2011). "The Tetramer Transformation," J. Immunol., 187:5-6.
Genbank, (2018). "Accession No. NM_010378.2; Mus musculus histocompatibility 2, class II antigen A, alpha (H2-Aa), mRNA," available online at <https://www.ncbi.nlm.nih.gov/nuccore/NM_010378.2>, 4 pages.
Genbank, (2018). "Accession No. NM_013488.2; Mus musculus CD4 antigen (Cd4), mRNA," available online at <https://www.ncbi.nlm.nih.gov/nuccore/NM_013488.2>, 4 pages.

(Continued)

Primary Examiner — Changhwa J Cheu
(74) Attorney, Agent, or Firm — Morrison & Foerster LLP

(57) ABSTRACT

The present disclosure provides variant major histocompatibility complex class II (MHCII) beta chains, as well as heterodimers and multimers including MHCII alpha chains and the variant MHCII beta chains. Also provided by the present disclosure are nucleic acids, expression cassettes, and expression vectors encoding the MHCII beta chains. The heterodimers and multimers of the present disclosure have a higher affinity for CD4 co-receptors than comparable reagents including wild type MHCII beta chains, and therefore are advantageous for use in methods of phenotyping or activating CD4+ T cells.

22 Claims, 10 Drawing Sheets
Specification includes a Sequence Listing.

(56) References Cited

OTHER PUBLICATIONS

Genbank, (2018). "Accession No. NP_996988.2; histocompatibility 2, class II antigen A, beta 1 precursor [Mus musculus]," available online at <https://www.ncbi.nlm.nih.gov/protein/NP_996988.2>, 3 pages.
Govern et al., (2010). "Fast on-rates allow short dwell time ligands to activate T cells," Proc. Natl. Acad. Sci. USA, 107:8724-8729.
Henikoff et al., (1992). "Amino acid substitution matrices from protein blocks," Proc. Natl. Acad. Sci. USA, 89:10915-10919.
Huang et al., (2016). "Detection, phenotyping, and quantification of antigen-specific T cells using a peptide-MHC dodecamer," Proc. Natl. Acad. USA, 113:E1890-1897.
International Search Report and Written Opinion for PCT Patent Application No. PCT/US 19/44605 mailed on Jan. 7, 2020, 15 pages.
Jonsson et al., (2016). "Remarkably low affinity of CD4/peptide-major histocompatibility complex class II protein interactions," Proc. Natl. Acad. Sci. USA, 113:5682-5687.
Jonsson et al., (2016). "Supporting Information: Remarkably low affinity of CD4/peptide-major histocompatibility complex class II protein interactions," Proc. Natl. Acad. Sci. USA, 113:5682-5687, 11 pages.
Kieback et al., (2016). "Thymus-Derived Regulatory T Cells are Positively Selected on Natural Self-Antigen through Cognate Interactions of High Functional Avidity," Immunity, 44:1114-26.
Martinez et al., (2015). "Lower Affinity T Cells are Critical Components and Active Participants of the Immune Response," Front. Immunol., 6:468, 10 pages.
Matsui et al., (1994). "Kinetics of T-cell receptor binding to peptide/I-Ek complexes: correlation of the dissociation rate with T-cell responsiveness," Proc. Natl. Acad. Sci USA, 91:12862-12866.
Moon et al., (2007). "Naive CD4(+) T cell frequency varies for different epitopes and predicts repertoire diversity and response magnitude," Immunity, 27:203-213.

Moon et al., (2009). "Tracking epitope-specific T cells," Nat. Protoc., 4:565-581, 27 pages.
Nelson et al., (2015). "T cell receptor cross-reactivity between similar foreign and self peptides influences naive cell population size and autoimmunity," Immunity, 42:95-107.
Nepom, (2012). "MHC Class II Tetramers," J. Immunol., 188:2477-2482.
Rees et al., (1999). "An inverse relationship between T cell receptor affinity and antigen dose during CD4+ T cell responses in vivo and in vitro," Proc. Natl. Acad. Sci. USA, 96:9781-9786.
Tubo et al., (2013). "Single naive CD4+ T cells from a diverse repertoire produce different effector cell types during infection," Cell, 153:785-796.
Tungatt et al., (2015). "Antibody stabilization of peptide-MHC multimers reveals functional T cells bearing extremely low-affinity TCRs," J. Immunol., 194:463-474.
UniProt, (2019). "Accession No. Q9TP17: MHC class II antigen beta chain," Available online at <https://www.uniprot.org/uniprot/Q9TP17>, 7 pages.
Wang et al., (2011). "Affinity maturation of human CD4 by yeast surface display and crystal structure of a CD4-HLA-DR1 complex," Proc. Natl. Acad. USA, 108:15960-15965.
Wang et al., (2012). "The structural basis of αγ T-lineage immune recognition: TCR docking topologies, mechanotransduction, and co-receptor function," Immunol. Rev., 250(1):102-119, 32 pages.
Wulfing et al., (2002). "Costimulation and endogenous MHC ligands contribute to T cell recognition," Nature Immunology, 3(1):42.
Xiong et al., (2001). "T cell receptor binding to a pMHCII ligand is kinetically distinct from and independent of CD4," J. Biol. Chem, 276:5659-5667.
Zhu et al., (2012). "The transcription factor T-bet is induced by multiple pathways and prevents an endogenous Th2 cell program during Th1 cell responses," Immunity, 37:660-673.
Locksley et al., (1993). "Helper T cells without CD4: control of leishmaniasis in CD4-deficient mice," Science, 261:1448-1451.
Rudolph et al., (2006). "How TCRs bind MHCs, peptides, and coreceptors," Ann. Rev. Immunol., 24:419-466.

\* cited by examiner

```
           137         142          148              158
W F R N G Q E E T V G V S S T Q L I R N G D W T F Q V L V M L E M T
W F R N G Q X E T V G X S S T Q L X R N G D W T F Q V X V M L E M T
tggttccggaatggccagnnagacggtgggnnntcatccacacagcttnnaggaatggactggacctccagtcnnngtcatgctggacatgacc
```

FIG. 3

Wild Type: WFRNGQEETVGVSSTQLIRNGDWTFQVLVM (SEQ ID NO:4)
RI:        WFRNGQAETVGMSSTQLIRNGDWTFQVWVM (SEQ ID NO:5)
RII:       WFRNGQEETVGISSTQLYRNGDWTFQVDVM (SEQ ID NO:6)

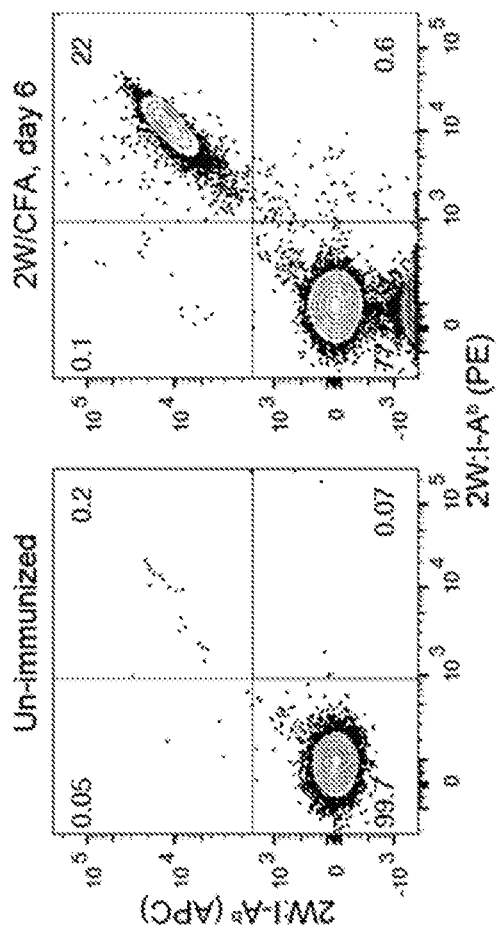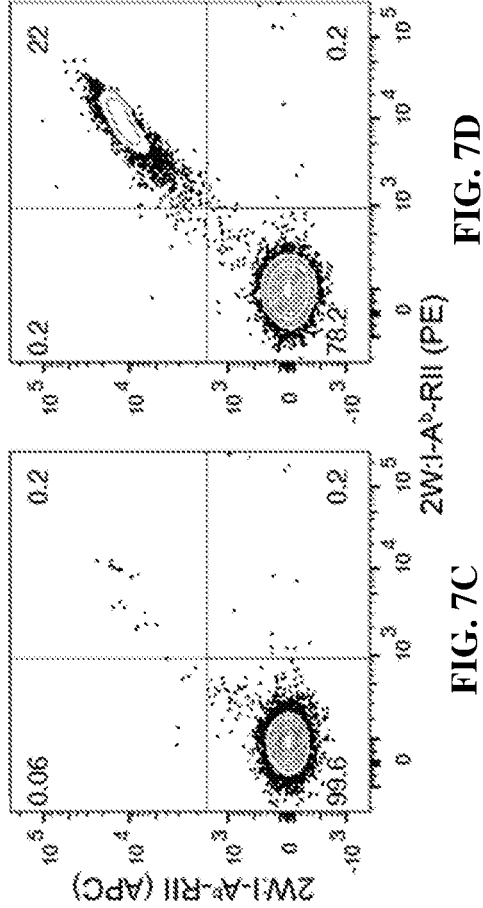

```
            131       *          *          *     160
I-Ab beta    WFRNGQEETV GVSSTQLIRN GDWTFQVLVM  (SEQ ID NO:4)
I-Af beta    WFRNGQEETV GVSSTQLIRN GDWTFQVLVM  (SEQ ID NO:4)
I-Ak beta    WFRNGQEETV GVSSTQLIRN GDWTFQVLVM  (SEQ ID NO:4)
I-Ef beta    WFRNGKEEKT GIVSTGLVRN GDWTFQTLVM  (SEQ ID NO:7)
I-Ek beta    WFRNGKEEKT GIVSTGLVRN GDWTFQTLVM  (SEQ ID NO:7)
consensus    WFRNGXXEXX GXXSTXLXRN GDWTFQXXVM  (SEQ ID NO:8)
             1                             30

CO-RECEPTOR AFFINITY ENHANCED MAJOR HISTOCOMPATIBILITY CLASS II MOLECULES

CROSS-REFERENCE TO RELATED APPLICATIONS

This application is a national phase application under 35 U.S.C. § 371 of International Application No. PCT/US2019/044605, filed Aug. 1, 2019, which claims priority to and benefit of U.S. Provisional Application No. 62/713,388, filed Aug. 1, 2018, the disclosure of each of which is incorporated herein by reference in its entirety.

STATEMENT REGARDING FEDERALLY SPONSORED RESEARCH OR DEVELOPMENT

This invention was made with government support under Grant No. R01-AI027998 awarded by the National Institutes of Health. The government has certain rights in the invention.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 144832000700SEQLIST.TXT, date recorded: Jan. 27, 2021, size: 20 KB).

TECHNICAL FIELD

The present disclosure relates generally to variant major histocompatibility complex class II (MHCII) beta chains, as well as heterodimers and multimers including MHCII alpha chains and the variant MHCII beta chains. The present disclosure also relates to nucleic acids, expression cassettes, and expression vectors encoding the MHCII beta chains. The heterodimers and multimers of the present disclosure are useful for phenotyping or activating $CD4^+$ T cells.

BACKGROUND $CD4^+$ T lymphocytes help vertebrates generate antigen-specific immunity to certain intracellular infections and cancers. The antigens recognized by T cell receptors (TCRs) on $CD4^+$ T cells are short peptides (p) embedded in the head regions of major histocompatibility complex class II molecules (MHCII) expressed by host dendritic cells, macrophages, and B cells. Because each nascent $CD4^+$ T cell expresses a unique TCR, each cell is likely to recognize a different MHCII-bound peptide. During infection, host cells generate microbial p:MHCII complexes, which are recognized by the rare $CD4^+$ T cells in the repertoire that by chance express complementary TCRs. The TCRs on these T cells bind the peptide-containing heads of the p:MHCII molecules, while their CD4 molecules simultaneously bind to the non-peptide-binding stalks (Rudolph et al., *Ann Rev Immunol*, 24:419-466, 2006). TCR and CD4 clustering engages signaling molecules then cooperate to trigger the T cells to divide and differentiate into effector cells that help B-lymphocytes or myeloid cells kill microbes.

Much of the information about the activation of polyclonal $CD4^+$ T cells has come from flow cytometry studies based on fluorescent p:MHCII tetramers (Doherty et al., *J Immunol*, 187:5-6, 2011). Although monomeric TCR-p:MHCII interactions have very low affinities (Corr et al., *Science*, 265:946-949, 1994; and Matsui et al., *Proc Natl Acad Sci USA*, 91:12862-12866, 1994), tetramerization of p:MHCII monomers can increase the avidity to the point where stable binding to TCRs can occur. When linked to fluorochromes, p:MHCII tetramers can be used to detect cognate $CD4^+$ T cells in a flow cytometer (Altman et al., *Science*, 274:94-96, 1996).

A significant limitation of the p:MHCII tetramer-based approach for use in flow cytometry is that it under samples $CD4^+$ T cells in the population bearing TCRs with low but biologically-relevant affinity for the peptide:MHCII ligand of interest (Martinez and Evavold, *Front Immunol*, 6:468, 2015). As such, the art needs p:MHCII tetramers capable of binding to $CD4^+$ T cells bearing low affinity TCRs

BRIEF SUMMARY

The present disclosure provides variant major histocompatibility complex class II (MHCII) beta chains, as well as heterodimers and multimers including MHCII alpha chains and the variant MHCII beta chains. Also provided by the present disclosure are nucleic acids, expression cassettes, and expression vectors encoding the MHCII beta chains. The heterodimers and multimers of the present disclosure have a higher affinity for CD4 co-receptors than comparable reagents including wild type MHCII beta chains, and therefore are advantageous for use in methods of phenotyping or activating $CD4^+$ T cells.

BRIEF DESCRIPTION OF THE DRAWINGS

FIG. 1A shows the region of the I-$A^b$ beta chain targeted for generation of the mutant library with the wild type amino acid sequence (in single letter code) set forth as SEQ ID NO:1 and the amino acid sequence of the library members set forth as SEQ ID NO:2, in which "X" at positions 137, 142, 148 and 158 represent any one of the 20 standard amino acid residues. The nucleic acid sequence of the library members is set forth as SEQ ID NO:3, with "nnn" representing the following 20 codons: AAA, AAC, ACT, ATC, ATG, CAG, CAT, CCG, CGT, CTG, GAA, GAC, GCT, GGT, GTT, TAC, TCT, TGC, TGG, and TTC. FIG. 1B shows a map of the pcDNA5/FRT plasmid. FIG. 1C shows an exemplary strategy for library generation. In the P5R:I-$A^b$ beta construct, N indicates the N-terminal portion of the I-$A^b$ beta chain, L indicates the segment targeted for mutagenesis, and C indicates the C-terminal portion of the I-$A^b$ beta chain including the transmembrane domain and cytoplasmic tail. The lighter colored bars in the L segment indicate the four amino acid residues that were targeted.

FIG. 2A shows flow cytometry plots of CHO cell populations stained with mouse CD4/streptavidin-APC tetramer, after the indicated rounds of enrichment with CD4/streptavidin-APC tetramer and APC antibody-conjugated magnetic beads. FIG. 2B shows flow cytometry plots of CD4/streptavidin-APC tetramer-stained CHO cells expressing wild-type P5R:I-$A^b$ molecules, or CHO clones expressing P5R:I-$A^b$-RI or P5R:I-$A^b$-RII molecules.

FIG. 3 shows a model of a CD4 affinity enhanced p:MHCII molecule binding to a TCR and CD4 molecule on a T cell membrane.

FIG. 5A is a scatter plot showing the number of CD4+ T cells detected with the indicated tetramers in the spleen and lymph nodes of individual naïve or day six Lm-P5R-infected B6 mice. Horizontal bars indicate means. Log transformed values from the indicated pairs were compared with an unpaired Students t-test. P values are shown. FIG. 5B shows representative flow cytometry contour plots of CD4+ T cells from the spleen and lymph nodes of individual naïve B6 mouse stained and enriched with the P5R:I-A$^b$ (top) or P5R:I-A$^b$-RII (bottom) tetramers. FIG. 5C shows flow cytometry contour plots of CD4+ T cells from the spleen and lymph nodes of individual day six Lm-P5R-infected B6 mouse stained and enriched with the indicated P5R:I-A$^b$ (top) or P5R:I-A$^b$-RII (bottom) tetramers. FIG. 5D shows flow cytometry contour plots of CD4+ T cells from the spleen and lymph nodes of individual naïve B6 mouse stained and enriched with the indicated 2W:I-A$^b$ (top) or 2W:I-A$^b$-RII tetramers (bottom).

FIG. 6A shows flow cytometry contour plots of CD4+ T cells from the spleen and lymph nodes of day six Lm-P5R-infected B6 mice stained and enriched with P5R:I-A$^b$ (APC) and P5R:I-A$^b$ (PE) tetramers. FIG. 6B shows flow cytometry contour plots of CD4+ T cells from the spleen and lymph nodes of day six Lm-P5R-infected B6 mice stained and enriched with P5R:I-A$^b$ (APC) and P5R:I-A$^b$-RII (PE) tetramers.

FIGS. 7A-D are flow cytometry contour plots showing detection of 2W:I-A$^b$-specific T cells in CD4-deficient mice. FIG. 7A is a flow cytometry contour plot of CD90+ T cells from the spleen and lymph nodes of naive Cd4$^{-/-}$ mice stained and enriched with 2W:I-A$^b$ tetramers. FIG. 7B is a flow cytometry contour plot of CD90+ CD8− T cells from the spleen and lymph nodes of day six 2W/CFA-primed Cd4$^{-/-}$ mice stained and enriched with 2W:I-A$^b$ tetramers. FIG. 7C is a flow cytometry contour plot of CD90+ CD8− T cells from the spleen and lymph nodes of naive Cd4$^{-/-}$ mice stained and enriched with 2W:I-A$^b$-RII tetramers. FIG. 7D is a flow cytometry contour plot of CD90+ CD8− T cells from the spleen and lymph nodes of day six 2W/CFA-primed Cd4$^{-/-}$ mice stained and enriched with 2W:I-A$^b$-RII tetramers.

FIG. 9 shows an alignment of the amino acid sequences of a portion of MHCII beta chains of several mouse alleles, along with a consensus sequence. Sequences of the three mouse I-A alleles (SEQ ID NO:4) in this region of the MHCII beta chain are identical, as are the sequences of the two mouse I-E alleles (SEQ ID NO:7). Asterisks indicate the amino acids targeted in the library of P5R:I-A$^b$ beta molecules. The E and L at positions 137 and 158 are conserved in all I-A and I-E isoforms while the V and I at positions 142 and 148 of the I-A isoforms have conservative substitutions of I and V, respectively, in the I-E isoforms. Positions not fully conserved between I-A and I-E alleles and/or positions targeted for substitution are designated with an "X" in the consensus sequence (SEQ ID NO:8). Preferred residues in the "X" positions are shown below the alignment.

DETAILED DESCRIPTION

The present disclosure provides variant major histocompatibility complex class II (MHCII) beta chains, as well as heterodimers and multimers including MHCII alpha chains and the variant MHCII beta chains. The present disclosure also provides nucleic acids, expression cassettes, and expression vectors encoding the MHCII beta chains. The heterodimers and multimers of the present disclosure have a higher affinity for CD4 co-receptors than comparable reagents including wild type MHCII beta chains, and are therefore advantageous for use in methods of phenotyping or activating CD4+ T cells.

A significant limitation of the p:MHCII tetramer-based approach for use in flow cytometry is that it under samples CD4+ T cells in the population bearing TCRs with low but biologically-relevant affinity for the peptide:MHCII ligand of interest (Martinez and Evavold, *Front Immunol*, 6:468, 2015). The inventors reasoned that this limitation could be related to the fact that p:MHCII tetramer-binding to the TCRs on CD4+ T cells is not aided by CD4 binding to the stalks of the MHCII molecules in the tetramer (Crawford et al., *Immunity*, 8:675-682, 1998), perhaps because CD4 binds to its target site with an exceedingly low affinity (Davis et al., *Nat Immunol*, 4:217-224, 2003; and Jonsson et al., *Proc Natl Acad Sci USA*, 113:5682-5687, 2016).

As described herein, this issue was addressed using directed evolution (Bloom et al., *Proc Natl Acad Sci USA*, 106(Suppl1):9995-10000, 2009) to select variant MHCII molecules that bind to CD4 much better than wild-type MHCII molecules. Importantly, the peptide-bound CD4 affinity-enhanced MHCII molecules (containing a variant MHCII beta chain) were found to be better than wild-type molecules at detecting CD4+ T cells with low affinity TCRs. This capacity allowed peptide-bound CD4 affinity-enhanced MHCII molecules to detect and activate specific CD4+ T cells in polyclonal repertoires more effectively than the comparable wild-type MHCII molecules. As such, the peptide-bound CD4 affinity-enhanced MHCII tetramers of the present disclosure are superior to conventional tetramers as flow cytometry reagents for detection of antigen-specific CD4+ T cells and could be used to create a new class of cellular vaccines targeted to CD4+ T cells with low affinity TCRs.

Figures 4A, 4B:
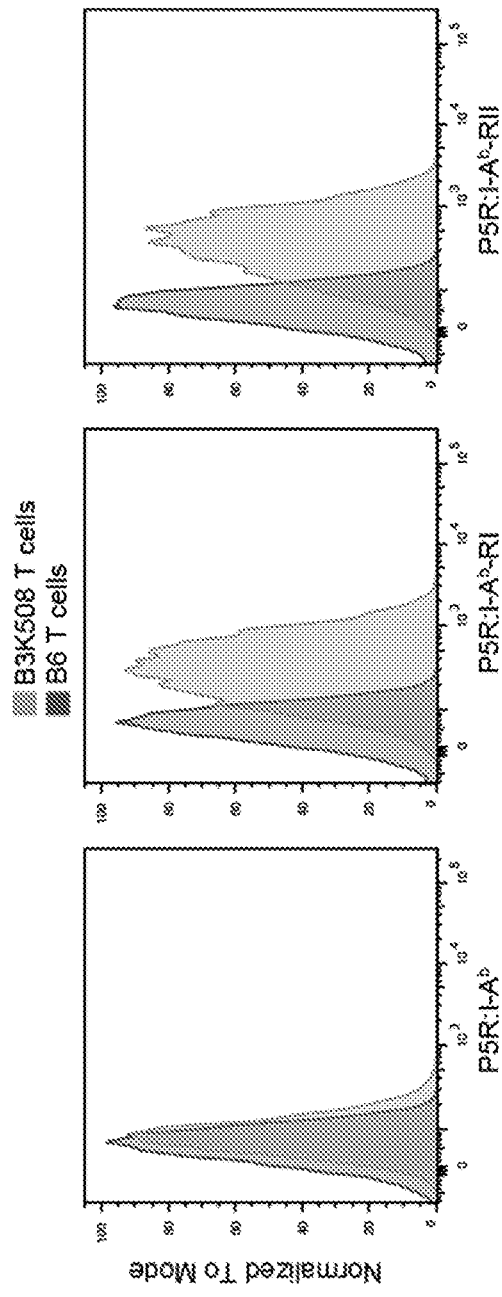
FIG. 4A shows the amino acid sequences of a portion of the I-$A^b$ beta chain of the wild type I-$A^b$ (SEQ ID NO:4), I-$A^b$-RI (SEQ ID NO:5) and I-$A^b$-RII (SEQ ID NO:6) tetramers.
FIG. 4B shows flow cytometry histograms of CD4+ T cells from polyclonal B6 (dark gray) or monoclonal B3K508 P5R:I-A$^b$-specific TCR transgenic mice (light gray) stained with the indicated tetramers.

Specifically, molecular evolution was used to select two exemplary I-A$^b$ molecules (I-A$^b$ is a mouse MHCII molecule) with substitutions at four putative CD4-binding positions in the I-A$^b$ beta chain that were capable of stable binding to a CD4 tetramer. CD4 affinity-enhanced p:I-A$^b$ molecule binding to CD4 must still be relatively weak, however, since soluble CD4 affinity-enhanced p:I-A$^b$ tetramers did not bind stably to CD4 molecules on the membranes of all CD4+ T cells, only CD4+ T cells with TCRs specific for the peptide-containing head (FIG. 4B). These results suggest that the superiority of CD4 affinity-enhanced p:I-A$^b$ tetramers at detecting CD4+ T cells with low affinity TCRs is because their improved but still transient binding to CD4 stabilizes weak interactions with nearby TCRs on the T cell membrane (FIG. 3).

Figure 5A:
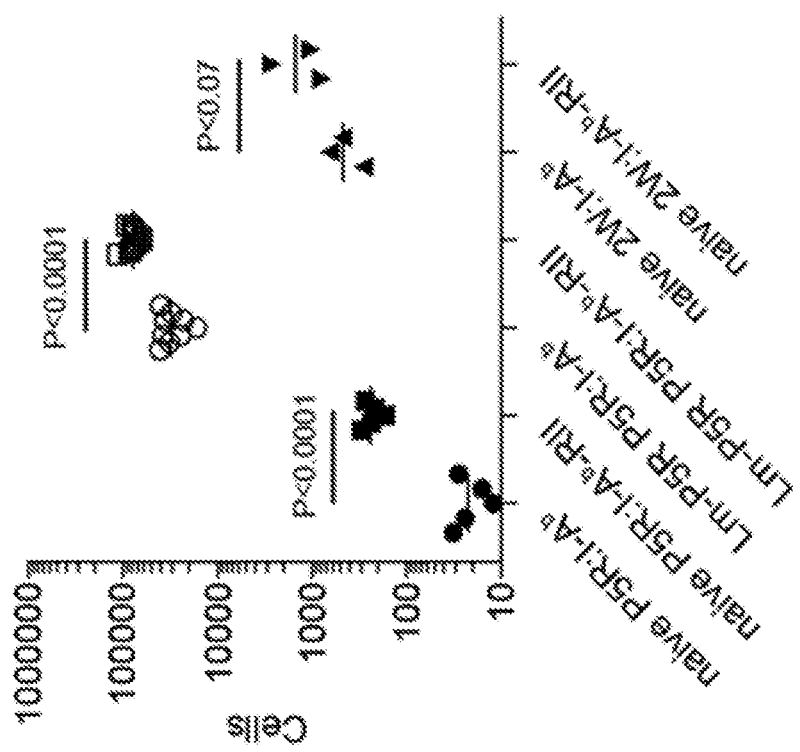
FIGS. 5A-5D show detection of polyclonal CD4+ T cells using p:I-A$^b$-RII tetramers.

CD4 affinity-enhanced I-A$^b$ tetramers containing foreign (non-mouse) peptides detected more naïve T cells than conventional p:I-A$^b$ tetramers in mice that were never exposed to the relevant foreign peptides (FIG. 5A). Although only two CD4 affinity-enhanced P5R:I-A$^b$ and 2W:I-A$^b$ tetramers were tested, it was notable that the fold increase over the number of cells detected with conventional p:I-A$^b$ tetramers was greater for the smaller P5R:I-A$^b$-specific population. Using conventional tetramers, a CD4$^+$ T cell population specific for an MHCII-bound non-mouse peptide was found to be small in mice because the mouse host expresses a similar peptide that causes intrathymic deletion of some cells in the population (Nelson et al., *Immunity,* 42:95-107, 2015). Since the deleted cells tended to have higher affinity TCRs, small foreign p:MHCII-specific populations were enriched for cells with low affinity TCRs. CD4 affinity-enhanced p:MHCII tetramers are expected to be especially useful for analysis of populations like these. This contention was tested using a peptide from mouse myelin oligodendrocyte glycoprotein (MOG peptide), which when bound to I-Ab is recognized by a CD4$^+$ T cell population in B6 mice that has been exposed to immune tolerance mechanisms including deletion of cells with high affinity TCRs (Kieback et al., *Immunity,* 44:1114-26, 2016). Again, the CD4 affinity-enhanced I-Ab tetramer containing MOG peptide detected more naïve T cells than the conventional I-Ab tetramers containing MOG peptide in mice (TABLE 1).

I. Definitions

To facilitate an understanding of the embodiments disclosed herein, a number of terms and phrases are defined below. Terms and abbreviations not defined should be accorded their ordinary meaning as used in the art.

As used herein and in the appended claims, the singular forms "a," "an," and "the" include plural references unless indicated otherwise. For example, "a" monocyte includes one or more monocytes.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting of" and "consisting essentially of" embodiments.

The term "about" as used herein in reference to a value, encompasses from 90% to 110% of that value (e.g., about 20 amino acids refers to 18 amino acids to 22 amino acids and includes 20 amino acids).

Numerical ranges are inclusive of the numbers defining the range (e.g., 18 to 22 amino acids encompasses 18, 19, 20, 21 and 22 amino acids.

The term "plurality" as used herein in reference to an object refers to three or more objects. For instance, "a plurality of multimers" refers to three or more multimers, preferably 3, 4, 5, 6, 7, 8, 9, 10, 100, 1,000, 10,000, 100,000, 1,000,000 or more multimers.

As used herein, the term "isolated" refers to an object (e.g., monocyte) that is removed from its natural environment (e.g., separated). "Isolated" objects are at least 50% free, preferably 75% free, more preferably at least 90% free, and most preferably at least 95% (e.g., 95%, 96%, 97%, 98%, or 99%) free from other components with which they are naturally associated.

The term "heterologous peptide" when used in connection with a MHCII beta chain refers to a peptide of 10 to 25 amino acids in length, which is not a fragment of the MHCII beta chain. In general, the heterologous peptide is bound in whole or in part in a peptide binding groove of a MHCII heterodimer comprising a MHCII alpha chain and a MHCII beta chain. In some embodiments, the heterologous peptide is greater than (lower limit) 9, 10, 11, 12, 13, 14, 15, 16, 17, 18, 19, or 20 amino acids in length. In some embodiments, the heterologous peptide is less than (upper limit) 26, 25, 24, 23, 22, 21, 20, 19, 18, 17, 16 or 15 amino acids in length. That is the length is in the range of from about 10 to about 25 in which the lower limit is less than the upper limit.

The term "variant" when used in connection with a MHCII beta chain refers to a MHCII beta chain with an amino acid sequence that differs from a reference wild type MHCII beta chain sequence, generally of the same genus or species (e.g., not 100% identical). Preferably heterodimers and multimers including a MHCII alpha chain and the variant MHCII beta chain are capable of binding the same heterologous peptides as comparable reagents including the reference wild type MHCII beta chain. More preferably, heterodimers and multimers including a MHCII alpha chain and the variant MHCII beta chain and binding a heterologous peptide have a higher affinity for CD4$^+$ T cells specific for the heterologous peptide than comparable reagents including the reference wild type MHCII beta chain.

In the context of two or more sequences (e.g., nucleic acid sequences or amino acid sequences) the terms "identical" and "identify" refer to the percentage of residues in a subject sequence that are identical to residues in a reference sequence, after aligning the sequences and introducing gaps, if necessary, to achieve the maximum percent sequence identity. Conservative substitutions are not considered as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

As used herein, the term "glycine-rich linker" refers to a peptide of about 5 to about 15 amino acids in length in which the majority of amino acids are glycine. For instance, a glycine rich linker that is 10 amino acids in length will include at least 6 glycine residues. Typically, the remaining residues in a glycine-rich linker include one or both of serine and threonine. In some embodiments, the glycine-rich linker is greater than (lower limit) 4, 5, 6, 7, 8 or 9 amino acids in length. In some embodiments, the glycine-rich linker is less than (upper limit) 16, 15, 14, 13, 12, 11 or 10 amino acids in length. That is the length is in the range of from about 5 to about 15 in which the lower limit is less than the upper limit.

II. Variant MHCII Beta Chains, Heterodimers and Multimers

The present disclosure provides variant major histocompatibility complex class II (MHCII) beta chains comprising an extracellular domain comprising an amino acid substitution in one or more positions selected from the group consisting of 137, 142, 148 and 158, wherein the positions are numbered in correspondence with the amino acid sequence of a wild type MHCII beta chain of SEQ ID NO:9.

In some embodiments, the amino acid substitution at position 137 is E137A. In some embodiments, the amino acid substitution at position 142 is V142M or V142I. In some embodiments, the amino acid substitution at position 148 is I148Y. In some embodiments, the amino acid substitution at position 158 is L158W or L158D. In some embodiments, the variant MHCII beta chain has at least 90%, 91%, 92%, 93%, 94%, 95%, 96%, 97%, 98% or 99% sequence identity to SEQ ID NO:7, SEQ ID NO:8, or SEQ ID NO:9. In some embodiments, the variant MHCII beta chain is an I-A$^b$ MHCII beta chain.

In some embodiments, the variant MHCII beta chain is a fusion protein further comprising a heterologous peptide of 10-25 amino acids in length and a glycine-rich linker of 10-15 amino acids in length at its amino-terminus. In some embodiments, the heterologous peptide is a P5R peptide, a 2W peptide, or a MOG peptide. In some embodiments, the variant MHCII beta chain lacks the transmembrane domain and cytoplasmic tail.

Also provided are heterodimers comprising a variant MHCII beta chain and a MHCII alpha chain. In some embodiments, the variant MHCII beta chain is a fusion protein further comprising a heterologous peptide of 10-25 amino acids in length and a glycine-rich linker of 10-15 amino acids in length at its amino-terminus. In some embodiments, the MHCII alpha chain has at least 90%, 91%, 92%, 93%, 94%, 95%, 96%, 97%, 98% or 99% sequence identity to SEQ ID NO:26. In some embodiments, the heterologous peptide is bound in a peptide-binding groove of the heterodimer. In some embodiments, the MHCII alpha chain lacks the transmembrane domain and cytoplasmic tail. In some embodiments, the heterodimers may be labeled with biotin.

In some embodiments, provided herein are multimers comprising two, three or four heterodimers comprising a variant MHCII beta chain and a MHCII alpha chain. In some embodiments, the multimer is a dimer, a trimer or a tetramer. In some embodiments, the multimer further comprises a fluorescent tag. In some embodiments, the fluorescent tag may include an APC, a FITC, or a PE. In some embodiments, the multimer further comprises streptavidin fluorochromes.

In some embodiments, the heterodimers and multimers of the present disclosure have a higher affinity for CD4 co-receptors than comparable wild type MHCII molecules. In some embodiments, the heterodimers and multimers of the present disclosure show improved binding to CD4$^+$ T cells with low affinity TCRs specific for the heterologous peptide than comparable wild type MHCII molecules. In some embodiments, the equilibrium dissociation constant of the low affinity TCRs for the heterologous peptide may be above 80 μM, such as above 81 μM, 83 μM, 85 μM, 87 μM, 89 μM, 91 μM, 93 μM, 95 μM, 97 μM, or 99 μM. In some embodiments, the heterodimers and multimers of the present disclosure do not show improved binding to CD4$^+$ T cells with low affinity TCRs which are not specific for the heterologous peptide as compared to wild type MHCII molecules. In some embodiments, the heterodimers and multimers of the present disclosure detect more CD4$^+$ T cells in the polyclonal repertoire than comparable wild type MHCII molecules. In some embodiments, the CD4$^+$ T cells are naïve CD4$^+$ T cells and/or effector CD4$^+$ T cells. In some embodiments, the heterodimers and multimers of the present disclosure compete with comparable wild type MHCII molecules for binding to TCRs specific for the heterologous peptide. In some embodiments, the heterodimers and multimers of the present disclosure activate CD4$^+$ T cells more effectively than comparable wild type MHCII molecules.

Algorithms that are suitable for determining percent sequence identity and sequence similarity are the BLAST and BLAST 2.0 algorithms, described in Altschul et al., *J Mol Biol*, 215: 403-410, 1990; and Altschul et al., *Nucleic Acids Res.* 25: 3389-3402, 1977, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915, 1989).

III. Nucleic Acids, Expression Cassettes and Vectors Encoding Variant MHCII Beta Chains, and Host Cells for Expression Thereof Nucleic Acid In some embodiments, the present disclosure provides a nucleic acid encoding a variant MHCII beta chain of any one of the preceding embodiments. In some embodiments, the present disclosure is related to a nucleic acid encoding a variant MHCII beta chain comprising an amino acid substitution in one or more positions selected from the group consisting of 137, 142, 148, and 158, where the positions are numbered in correspondence with the amino acid sequence of a wild type MHCII beta chain of SEQ ID NO:9. The nucleic acid encoding a variant MHCII beta chain of the present disclosure may be of any nucleic acid type, including RNA, such as messenger RNA (mRNA), and DNA, such as complementary DNA (cDNA), genomic DNA (gDNA), and synthetic DNA.

Expression Cassette

In another aspect, the present disclosure provides an expression cassette comprising a promoter operably linked to a nucleic acid encoding a variant MHCII beta chain of any of the preceding embodiments. As used herein, an "expression cassette" refers to a nucleic acid construct that, when introduced into a host cell, results in one or both of RNA transcription and polypeptide translation. The promoter may be heterologous to the nucleic acid. In some embodiments, the promoter may be inducible, while in other embodiments the promoter may be constitutive.

Expression Vector

In some embodiments, the present disclosure provides for expression vectors comprising an expression cassette of any one of the preceding embodiments. As used herein, an "expression vector" refers to a vehicle for introducing foreign nucleic acid into a host cell. In addition to the expression cassette, the expression vector comprises one or more of an origin of replication, a multiple cloning site, and a selectable marker (e.g., antibiotic resistance gene). Suitable expression vectors include but are not limited to plasmids and viruses (e.g., lentiviruses, retroviruses, adenoviruses, and adeno-associated viruses). In some preferred embodiments, the expression vector is a plasmid.

Host Cells

In some embodiments, the present disclosure provides host cells comprising an expression cassette or expression vector of any one of the preceding embodiments. In some embodiments, the host cell is a prokaryotic cell. In other embodiments, the host cell is an eukaryotic cell. In some embodiments, the host cell is a bacterial cell, an insect cell, or a mammalian cell.

Method of Producing a Variant MHCII Heterodimer

Also provided is a method of producing a variant MHCII heterodimer with a higher affinity for CD4, comprising: (a) generating a library of DNA molecules encoding a fusion protein comprising a heterologous peptide linked to the amino terminus of a mature form of a variant MHCII beta chain via a glycine-rich linker, wherein the variant MHCII beta chain encoded by each DNA molecule of the library comprises one or more target positions selected from the group consisting of 137, 142, 148 and 158, the target positions are numbered in correspondence with the amino acid sequence of a wild type MHCII beta chain of SEQ ID NO:9, and the target positions may be any one of twenty possible amino acids while remaining positions are identical in sequence to a parent MHCII beta chain; (b) transfecting the DNA molecules of the library into mammalian host cells expressing a mature form of a MHCII alpha chain; (c) incubating the transfected host cells under conditions suitable for expression of a MHCII heterodimer on the cell surface, wherein the MHCII heterodimer comprises the heterologous peptide bound to a peptide binding groove formed upon association of the variant MHCII beta chain and the MHCII alpha chain; and (d) isolating transfected host cells that bind to CD4 tetramers with a higher affinity than control host cells expressing a MHCII heterodimer comprising the heterologous peptide bound to a peptide binding groove formed upon association of the parent MHCII beta chain and the MHCII alpha chain.

In some embodiments, the parent MHCII beta chain is an I-$A^b$ beta chain. In some embodiments, the MHCII alpha chain is an I-$A^b$ alpha chain. In some embodiments, each of the mammalian host cell displays a single MHCII alpha/beta heterodimer with a different combination of amino acid substitutions at the targeted four positions of the beta chain.

IV. Compositions, Articles of Manufacture and Kits Including Multimers

The present disclosure further provides compositions comprising a plurality of multimers of any one of the preceding embodiments. The present disclosure also provides compositions comprising a plurality of multimers and an isotonic solution. In some embodiments, the isotonic solution is a normal saline. In some embodiments, the isotonic solution is a physiologically acceptable buffer such as phosphate buffered saline. In some embodiments, the isotonic solution does not include antibiotics.

The present disclosure further provides a kit comprising a composition comprising a plurality of multimers of any one of the preceding embodiments, an isotonic solution, and instructions for use of the composition to assess binding of the multimers to $CD4^+$ T cells specific for the heterologous peptide. In some embodiments, binding of the multimers to $CD4^+$ T cells specific for the heterologous peptide is assessed by flow cytometry.

The present disclosure further provides an article of manufacture comprising a solid support to which a plurality of the heterodimers of any one of the preceding embodiments are affixed. In some embodiments, the solid support is tissue culture ware selected from the group consisting of a dish, a flask, and a multi-well plate.

V. Methods of Use of Multimers

The present disclosure further provides a method for assessing $CD4^+$ T cell frequency, comprising contacting a sample comprising a plurality of $CD4^+$ T cells with a composition comprising a plurality of multimers of any one of the preceding embodiments, under conditions suitable for binding $CD4^+$ T cells specific for the heterologous peptide to the multimers. In some embodiments, the $CD4^+$ T cell frequency is assessed by flow cytometry immunofluorescence assay.

Also provided is a method for activating T cells, comprising incubating a sample comprising a plurality of T cells in culture medium in the tissue culture ware as described in section IV above, under conditions suitable for activating T cells specific for the heterologous peptide. In some embodiments, the tissue culture medium comprises interleukin-2 (IL-2). In some embodiments, T cell activation is assessed using one or more markers of TCR signaling.

In some embodiments, the multimers provided by the present disclosure also find use as flow cytometry reagents for detection of antigen-specific $CD4^+$ T cells. In some embodiments, the multimers provided by the present disclosure may be used to create cellular vaccines targeted to $CD4^+$ T cells with low affinity TCRs.

ENUMERATED EMBODIMENTS

The following enumerated embodiments are representative of some aspects of the invention.

1. A variant major histocompatibility complex class II (MHCII) beta chain comprising an extracellular domain comprising an amino acid substitution in one or more positions selected from the group consisting of 137, 142, 148 and 158, wherein the positions are numbered in correspondence with the amino acid sequence of a wild type MHCII beta chain of SEQ ID NO:9

2. The variant MHCII beta chain of embodiment 1, wherein the amino acid substitution:
   at position 137 is E137A;
   at position 142 is V142M or V142I;
   at position 148 is I148Y; and/or
   at position 158 is L158W or L158D; and
   and wherein the variant has at least 90% sequence identity to SEQ ID NO:7, SEQ ID NO:8, or SEQ ID NO:9.

3. The variant MHCII beta chain of embodiment 1 or 2, comprising E137A, V142M, and L158W.

4. The variant MHCII beta chain of embodiment 3, comprising the amino acid sequence of SEQ ID NO:5.

5. The variant MHCII beta chain of embodiment 1 or 2, comprising V142I, I148Y, and L158D.

6. The variant MHCII beta chain of embodiment 5, comprising the amino acid sequence of SEQ ID NO:6.

7. The variant MHCII beta chain of any one of embodiments 1-6, wherein the variant is a fusion protein further comprising a heterologous peptide of 10 to 25 amino acids in length and a glycine-rich linker of 10 to 15 amino acids in length at its amino-terminus.

8. A heterodimer comprising the variant MHCII beta chain of embodiment 7, and a MHCII alpha chain, wherein the MHCII alpha chain has at least 90% sequence identity to SEQ ID NO:26, and wherein the heterologous peptide is bound in a peptide-binding groove of the heterodimer.

9. A multimer comprising two, three or four heterodimers of embodiment 8, optionally wherein the multimer is a dimer, trimer, or tetramer.

10. The multimer of embodiment 9, wherein the multimer further comprising a fluorescent tag, optionally wherein the fluorescent tag is APC, FITC or PE.

11. A nucleic acid encoding the variant MHCII beta chain of any one of embodiments 1-7.

12. An expression cassette comprising the nucleic acid of embodiment 11 in operable combination with a promoter.

13. An expression vector comprising the expression cassette of embodiment 12 and an antibiotic resistance gene, optionally wherein the expression vector is a plasmid.

14. A host cell comprising the expression vector of embodiment 13, optionally wherein the host cell is a bacterial cell, insect cell, or mammalian cell.

15. A composition comprising a plurality of multimers of embodiment 9 or 10 and an isotonic solution.

16. A kit comprising the composition of embodiment 15, and instructions for use of the composition to assess binding of the multimers to $CD4^+$ T cells specific for the heterologous peptide.

17. A method for assessing $CD4^+$ T cell frequency, comprising contacting a sample comprising a plurality of $CD4^+$ T cells with the composition of embodiment 15 under conditions suitable for binding $CD4^+$ T cells specific for the heterologous peptide to the multimers.

18. The method of embodiment 17, wherein $CD4^+$ T cell frequency is assessed by flow cytometry immunofluorescence assay.

19. The method of embodiment 18, further comprising contacting the sample with a monoclonal antibody specific for a cell surface marker under conditions suitable for binding $CD4^+$ T cells expressing the surface marker.

20. An article of manufacture comprising a solid support to which a plurality of the heterodimers of embodiment 8 are affixed.

21. The article of manufacture of embodiment 20, wherein the solid support is tissue culture ware selected from the group consisting of a dish, a flask, and a multi-well plate.

22. A method for activating T cells, comprising incubating a sample comprising a plurality of T cells in culture medium in the tissue culture ware of embodiment 21 under conditions suitable for activating T cells specific for the heterologous peptide.

23. The method of embodiment 22, wherein the tissue culture medium comprises interleukin-2 (IL-2).

24. A method for producing a variant MHCII heterodimer with a higher affinity for CD4, comprising:
(a) generating a library of DNA molecules encoding a fusion protein comprising a heterologous peptide linked to the amino terminus of a mature form of a variant MHCII beta chain via a glycine-rich linker, wherein
the variant MHCII beta chain encoded by each DNA molecule of the library comprises one or more target positions selected from the group consisting of 137, 142, 148 and 158,
the target positions are numbered in correspondence with the amino acid sequence of a wild type MHCII beta chain of SEQ ID NO:9, and
the target positions may be any one of twenty possible amino acids while remaining positions are identical in sequence to a parent MHCII beta chain,
(b) transfecting the DNA molecules of the library into mammalian host cells expressing a mature form of a MHCII alpha chain;
(c) incubating the transfected host cells under conditions suitable for expression of a MHCII heterodimer on the cell surface, wherein
the MHCII heterodimer comprises the heterologous peptide bound to a peptide binding groove formed upon association of the variant MHCII beta chain and the MHCII alpha chain; and
(d) isolating transfected host cells that bind to CD4 tetramers with a higher affinity than control host cells expressing a MHCII heterodimer comprising the heterologous peptide bound to a peptide binding groove formed upon association of the parent MHCII beta chain and the MHCII alpha chain.

EXAMPLES

The present disclosure is described in further detail in the following examples which are not in any way intended to limit the scope of the disclosure as claimed. The attached figures are meant to be considered as integral parts of the specification and description of the disclosure. The following examples are offered to illustrate, but not to limit the claimed disclosure.

In the experimental disclosure which follows, the following abbreviations apply: APC (allophycocyanin); FITC (fluorescein isothiocyanate); Lm (*Listeria monocytogenes*); MHC (major histocompatibility complex); MHCII (MHC class II); PBMC (peripheral blood mononuclear cells); PE (phycoerythrin); and TCR (T cell receptor).

Example 1: Co-Receptor Affinity-Enhanced Major Histocompatibility Class II Molecules This example describes the production of p:MHCII molecules with improved CD4 binding, and characterization thereof.

Materials and Methods

Mice. C57BL/6 (B6) and $Cd4^{-/-}$ mice were purchased from the Jackson Laboratory or the National Cancer Institute Mouse Repository. Eric Huseby (University of Massachusetts) provided the B3K508 $Rag^{-/-}$ mice. Jeff Zhu (NIH) provided the $Tbx21^{ZsGreen}$ B6 mice (Zhu et al., *Immunity*, 37: 660-673, 2012). Mice were housed in specific pathogen-free conditions at the University of Minnesota. All experiments were conducted in accordance with institutional and federal guidelines.

Infections and immunizations. Mice were injected intravenously with $10^7$ actA-deficient *Listeria monocytogenes* (Lm) bacteria engineered to secrete a fusion protein containing the P5R peptide (Lm-P5R) (Tubo et al., *Cell*, 153: 785-796, 2013). Mice were immunized via subcutaneous tail base injection of 10 μg of 2W peptide or MOG peptide emulsified in 50 μl of CFA.

Production of CHO cells stably expressing I-A$^b$ alpha chain. The Flp-In-CHO cell line (Thermo Fisher) was grown in Ham's F12 media (Thermo Fisher) supplemented with 10% fetal bovine serum (FBS), 2 mM L-glutamine, 1% Pen-Strep and 100 μg/mL Zeocin (Thermo Fisher). A sequence encoding the full-length I-A$^b$ alpha chain (NCBI Reference Sequence: NM_010378.2) was cloned into the pcDNA3.1-Neo vector (Invitrogen) and transfected into Flp-In CHO cells using Lipofectamine (ThermoFisher). Two days after transfection, cells were washed once with PBS and complete Ham's media containing 1 mg/ml G418 geneticin (Thermofisher) was added. Resistant cells expressing the I-A$^b$ alpha chain were selected and expanded for further co-transfection with the I-A$^b$ beta chain library as described below.

Molecular evolution of the I-A$^b$ beta chain. A library of I-A$^b$ beta chains with random substitutions in the codons for amino acids 137, 142, 148, and 158 (FIG. 1A) was generated using standard molecular biology techniques. Briefly, the pcDNA5/FRT vector (Thermo Fisher) (FIG. 1B) was linearized with HindIII (NEB) and gel purified. An 850 bp gene block (Gene block A shown below) containing coding sequences for the N-terminal (with the P5R peptide coding sequence at the terminus) and C-terminal flanking regions with an NsiI restriction site in the middle and 15 bp overlapping segments at the ends was obtained from Integrated DNA Technologies.

Gene Block A:

(SEQ ID NO: 10)
```
GTTTAAACTTAAGCTTATGGCTCTGCAGATCCCCAGCCTCCTCCTCTCA

GCTGCTGTGGTGGTGCTGATGGTGCTGAGCAGCCCCGGGACTGAGGGCG

GAGATTCCGAGGCCCAGAAGGCCCGCGCCAACAAGGCCGTGGACAAGGC

CGGCGGCGGAGGTACTAGTGGCGGTGGAAGTGGAGGGTCTGAAAGGCAT

TTCGTGTACCAGTTCATGGGCGAGTGCTACTTCACCAACGGGACGCAGC

GCATACGATATGTGACCAGATACATCTACAACGGGAGGAGTACGTGCG

CTACGACAGCGACGTGGGCGAGCACCGCGCGGTGACCGAGCTGGGCCGG

CCAGACGCCGAGTACTGGAACAGCCAGCCGGAGATCCTGGAGCGAACGC

GGGCCGAGCTGGACACGGTGTGCAGACACAACTACGAGGGGCCGGAGAC

CCACACCTCCCTGCGGCGGCTTGAACAGCCCAATGTCGTCATCTCCCTG

TCCAGGACAGAGGCCCTCAACCACCACAACACTCTGGTCTGCTCAGTGA

CAGATTTCTACCCAGCCAAGATCAAAGTGCGCTGGTTCCGGAATGGCCA

GATGCATGTCATGCTGGAGATGACCCCTCGGCGGGAGAGGTCTACACC

TGTCACGTGGAGCATCCCAGCCTGAAGAGCCCCATCACTGTGGAGTGGA

GGGCACAGTCTGAGTCTGCCTGGAGCAAGATGTTGAGCGGCATCGGGGG

CTGCCGTGCTTGGGGTGATCTTCCTCGGGCTTGGCCTTTTCATCCGTCAC

AGGAGTCAGAAAGGACCTCGAGGCCCTCCTCCAGCAGGGCTCCTGCAGT

GAAGCTTGGTACCGAGC.
```

Figures 1A, 1B, 1C:
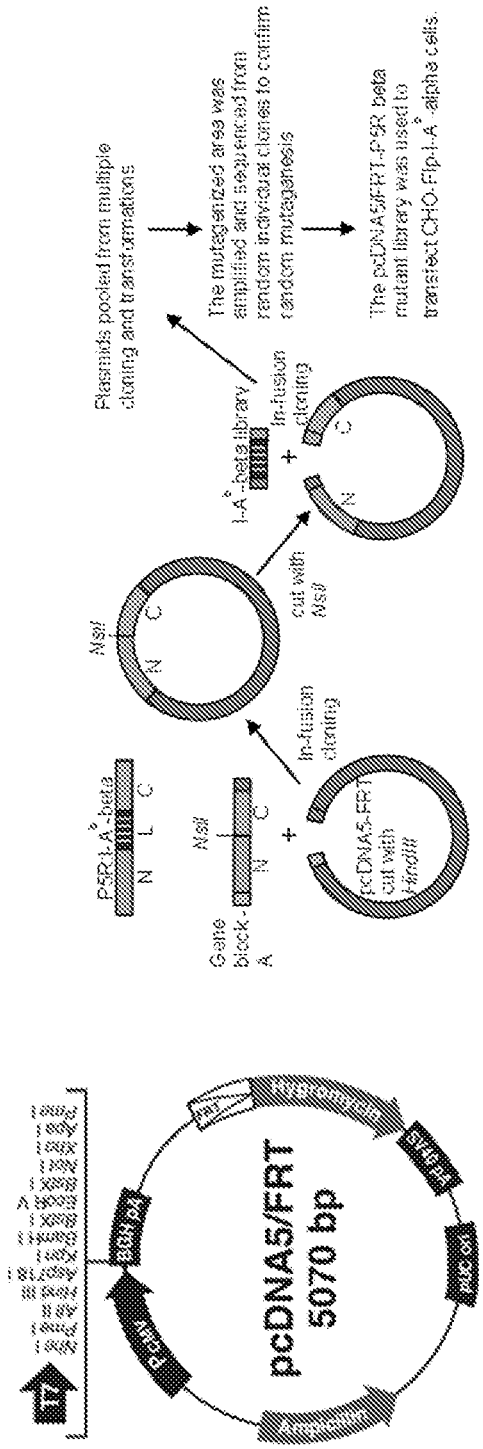
FIGS. 1A-1C show the generation of a P5R:I-$A^b$ beta mutant library.
Figure 2A:
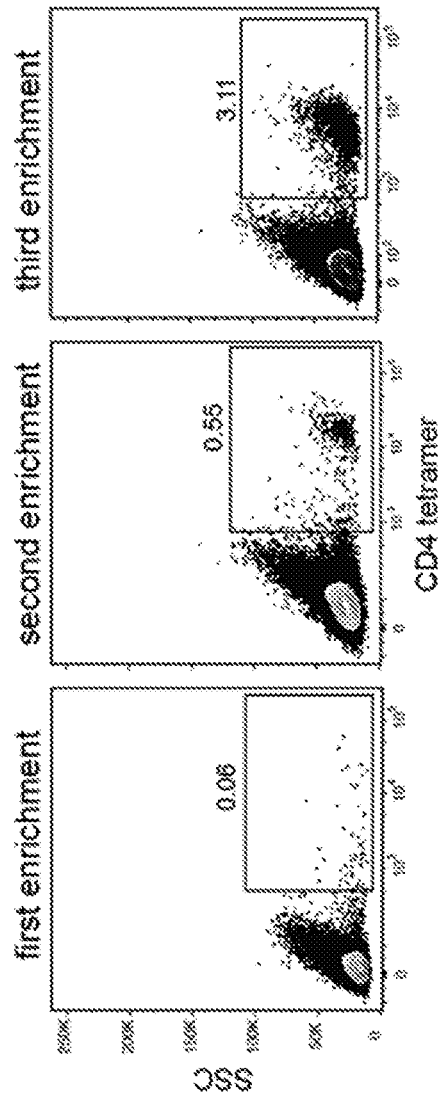
FIGS. 2A-2B show the selection of CHO cells expressing P5R:I-$A^b$ molecules with mutations at positions 137, 142, 148, and 158.
Figure 2B:
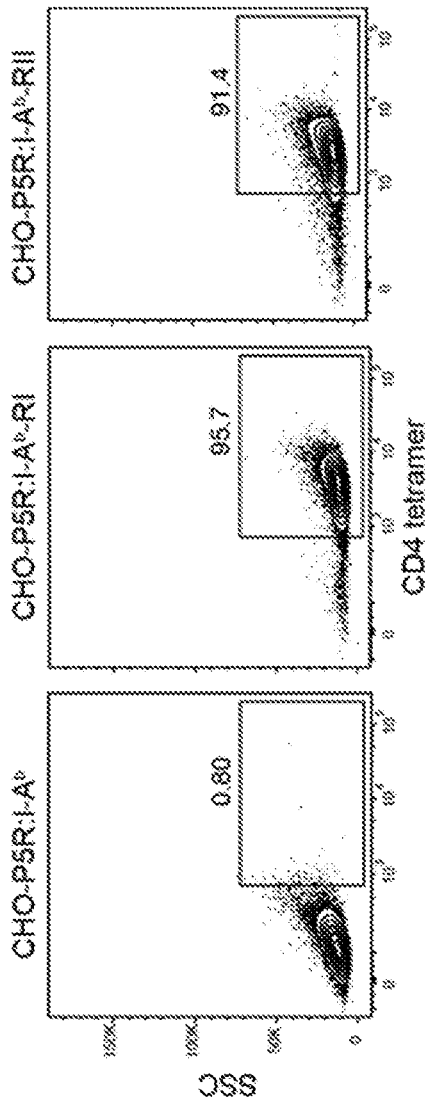

Gene Block A was cloned into the HindIII-digested pcDNA5/FRT vector using In-Fusion cloning (Takara Bio USA) (FIG. 1C). The resulting construct was sequence verified and linearized with NsiI, gel purified and PCR amplified with forward primer: 5'-GTCATGCTGG AGATGACCCC TCGG-3'(SEQ ID NO:11) and reverse primer 5'-CTGGCCATTC CGGAACCAGC G-3' (SEQ ID NO:12) to generate 17 bp overlaps for In-Fusion cloning of inserts containing the library. Single stranded oligonucleotides randomized at the indicated positions in FIG. 1A were obtained from Integrated DNA Technologies and converted to double stranded DNA with a reverse primer 5'-GT-CATCTCCA GCATGAC-3' (SEQ ID NO:13). Seventeen bp overlapping regions (FIG. 1A) at the ends were included in this 100 bp fragment for In-Fusion cloning (FIG. 1C) into the vector generated above. The fused products were transformed into Stellar competent *Escherichia coli* cells (Takara Bio USA). Transformants were selected on carbenicillin-containing plates. Plasmids from several *E. coli* clones were sequenced to confirm mutagenesis of the targeted sites. Plasmids were then isolated from the collection of *E. coli* cells and co-transfected with the pOG44 plasmid encoding flippase into a CHO cell line containing a single FRT target site and stably expressing the I-A$^b$ alpha chain. Transfectants were selected by growth in hygromycin (500 μg/ml). During selection, flippase recombined the FRT site flanked DNA molecules encoding P5R:I-A$^b$ beta chains into the FRT target site, one recombination per cell. The transfected population was then enriched for cells capable of binding to a mouse CD4/streptavidin-allophycocyanin (APC) tetramer using APC-conjugated magnetic beads (FIG. 2A). Tetramer-binding single cells were then sorted by flow cytometry and their P5R:I-A$^b$ beta chain DNA sequences were determined. Two clones, P5R:I-A$^b$-RI and P5R:I-A$^b$-RII were chosen for further study (FIG. 2B).

CD4 Tetramer generation. Regions encoding the signal peptide and the extracellular domain from Cd4 cDNA ORF Clone (Sino Biological, Catalog No. MG50134-CH, *NCBI Reference Sequence*: NM_013488.2) were amplified using: forward primer TD/mu.CD4-EcoR1-for: 5'-CCCCCGAATT CATGTGCCGA GCCATCTCTC TTA-3' (SEQ ID NO:14) and reverse primer TD/mu.CD4-Sal1-rev: 5'-CCCCCGTCGA CTTAATGATG ATGATGATGA TGTT-CATGCC ATTCAATTTT CTGCGCTTCA AAAATATCGT TCAGGCCGCT GCCGCCGCTG CCGCCTGTCT GGTT-CACCCC TCTGGAT-3' (SEQ ID NO:15) using Platinum Pfx DNA Polymerase (Thermo Fisher). The reverse primer was designed to code for an AVI tag followed by a 6× His tag (Hochuli et al. *J. Chromatogr.*, 411: 177-184, 1987). The 1,288 bp amplicon was purified using MinElute PCR purification kit (Qiagen) and double digested with EcoRI (NEB) and Sal1(NEB) in CutSmart buffer. Purified restriction digested insert was ligated to similarly digested and purified pRMHa3 vector (Bunch et al. *Nucl. Acids Res.*, 16: 1043-1061, 1988) using T4 DNA ligase (Thermo Fisher). The sequence verified construct of mu.CD4-pRMHa3 was co-transfected into *Drosophila* S2 cells with p18-BirA ligase and pCO-Blast plasmids. Transfection, selection, culture scale up, induction, purification and tetramerization were done as described below for p:MHCII tetramer generation.

p:MHCII tetramers. P5R:I-A$^b$, P5R:I-A$^b$-RI, P5R:I-A$^b$-RII, 2W:I-A$^b$, 2W:I-A$^b$-RII, MOG peptide:I-A$^b$, and MOG peptide:I-A$^b$-RII tetramers were produced as follows. Sequences encoding a single cistron with a signal peptide (SEQ ID NO:20), the P5R, 2W or MOG peptides, a flexible linker, the I-A$^b$ (wild type, RI or RII) beta chain sequences lacking the transmembrane domain and cytoplasmic tail, a basic leucine zipper domain, and a 6× His tag in N-terminal to C-terminal order were inserted into the pRMHa-3 vector with an upstream metallothionein promoter. These constructs were co-transfected into *Drosophila* S2 cells via calcium phosphate with a pRMHa-3-based plasmid encoding a single cistron with a signal peptide, the I-A$^b$ alpha chain lacking the transmembrane domain and cytoplasmic tail, an acidic leucine zipper domain, BirA biotinylation signal sequence (Beckett et al. *Protein Sci.,* 8: 921-929, 1999), and a 6× His tag in N- to C-terminal order, along with another plasmid encoding a blasticidin resistance gene at a molar ratio of 9:9:1. Transfected cells were selected in blasticidin-containing media and induced with copper sulfate as described (Moon et al. *Immunity,* 27: 203-213, 2007). Biotin-labeled p:I-A$^b$-RI beta/I-A$^b$ alpha and p:I-A$^b$-RII beta/I-A$^b$ alpha heterodimeric monomers (referred to as p:I-A$^b$-RI and p:I-A$^b$-RII) were purified from culture supernatants using nickel NTA and monovalent avidin columns as described (Nelson et al. *Immunity,* 42: 95-107, 2015). Biotin-labeled monomers (P5R:I-A$^b$, P5R:I-A$^b$-RI, P5R:I-A$^b$-RII, 2W:I-A$^b$, 2W:I-A$^b$-RII, MOG peptide:I-A$^b$, and MOG peptide:I-A$^b$-RII) monomers were formed into tetramers by mixing in a 4:1 ratio with PE- or APC-conjugated streptavidin (Prozyme).

P5R:I-A$^b$ Beta Chain Sequence:

(SEQ ID NO: 16)
MALQIPSLLLSAAVVVLMVLSSPGTEGEAQKARANKAVDKAGGGGTSGG

GSGGSERHFVYQFMGECYFTNGTQRIRYVTRYIYNREEYVRYDSDVGEH

RAVTELGRPDAEYWNSQPEILERTRAELDTVCRHNYEGPETHTSLRRLE

QPNVVISLSRTEALNHHNTLVCSVTDFYPAKIKVRWFRNGQEETVGVSS

TQLIRNGDWTFQVLVMLEMTPRRGEVYTCHVEHPSLKSPITVEWRAQSE

SAWSKGGGGSTTAPSAQLKKKLQALKKKNAQLKWKLQALKKKLAQHHHH

HH.

I-A$^b$ Alpha Chain Sequence:

(SEQ ID NO: 17)
MPCSRALILGVLALTTMLSLCGGEDDIEADHVGTYGISVYQSPGDIGQY

TFEFDGDELFYVDLDKKETVWMLPEFGQLASFDPQGGLQNIAVVKHNLG

VLTKRSNSTPATNEAPQATVFPKSPVLLGQPNTLICFVDNIFPPVINIT

WLRNSKSVADGVYETSFFVNRDYSFHKLSYLTFIPSDDDIYDCKVEHWG

LEEPVLKHWEPEIPAPMSELTETGGGGSTTAPSAQLEKELQALEKENAQ

LEWELQALEKELAQGGSGGSGLNDIFEAQKIEWHE.

In vitro T cell activation. Tissue culture plates were coated with streptavidin, then biotin-labeled P5R:I-A$^b$ or P5R:I-A$^b$-RI monomers. About 5×10$^5$ T cells purified from the spleen and lymph nodes of B3K508 Rag$^{-/-}$ transgenic mice using Miltenyi CD4$^+$ T cell selection kits were then added and the plates incubated overnight at 37° C. The cells were suspended the next day before staining with an anti-CD69 antibody.

Cell enrichment and flow cytometry. Trypsin was used to release CHO cells expressing P5R:I-A$^b$, P5R:I-A$^b$-RI, or -P5R:I-A$^b$-RII molecules from tissue culture flasks. The cells were then stained with 10 nM CD4 tetramer linked to streptavidin-PE or streptavidin-APC.

Single cell suspensions of spleen and lymph nodes from B3K508 mice were incubated in complete medium containing 50 nM dasatinib (Tungatt et al. *J. Immunol.,* 194: 463-474, 2015) for 20 minutes at 37° C. in a final volume of 400 µl per sample and P5R:I-A$^b$, P5R:I-A$^b$-RI, or P5R:I-A$^b$-RII tetramers linked to streptavidin-PE were added directly at a final concentration of 10 nM and incubated at 37° C. for an additional 45 minutes. The samples were washed with cold PBS plus 4% FBS and stained with antibodies against surface markers and GhostDye Red 780 viability dye (Tonbo Biosciences).

Single cell suspensions of spleen and lymph nodes from B6, or Cd4$^{-/-}$ mice were stained for 45 min at 37° C. temperature with P5R:I-A$^b$-RI, P5R:I-A$^b$-RI, P5R:I-A$^b$-RII, 2W:I-A$^b$, 2W:I-A$^b$-RI, or 2W:I-A$^b$-RII tetramers linked to streptavidin-PE or streptavidin-APC in buffer containing 50 nM dasatinib as described above. The samples were then mixed with magnetic beads conjugated with PE or APC antibodies and enriched for bead-bound cells on magnetized columns. A portion was removed for bead-based counting as described (Moon et al. *Nat. Protoc.,* 4: 565-581, 2009). The samples then underwent surface staining on ice with a mixture of antibodies specific for B220 (RA3-6B2), CD11b (MI-70), CD11c (N418), CD8a (5H10-1; Caltag), CD4 (RM4-5), or CD90 in the case of Cd4$^{-/-}$ mice, and CD44 (IM7), each conjugated with a different fluorochrome.

B3K508 T cells cultured overnight with plate-bound P5R:I-A$^b$ or P5R:I-A$^b$-RI monomers were stained with CD4 and CD69 antibodies labeled with different fluorochromes and with GhostDye Red 780 viability dye.

In all cases, stained cells were analyzed on an LSR II or Fortessa (Becton Dickinson) flow cytometer. Data were analyzed with FlowJo software (TreeStar).

Results

Generation of CD4 affinity-enhanced MHCII molecules. The I-A$^b$ MHCII molecule of the C57BL/6 (B6) mouse strain was used as the basis for a directed evolution approach to select MHCII molecules with enhanced CD4 binding. MHCII molecules are heterodimers composed of non-covalently linked alpha and beta chains tethered to the cell surface by transmembrane domains (Rudolph et al., *Annu. Rev. Immunol.,* 24: 419-466, 2006). The amino acids at positions E137, V142, I148, and L158 of the MHCII beta 2 domain are thought to form part of the CD4 binding site (Jonsson et al., *Proc. Natl. Acad. Sci. USA,* 113: 5682-5687, 2016) while amino acids from the alpha 1 and beta 1 domains form the peptide-binding groove, which interacts with TCRs (Rudolph et al., supra, 2006). A library of pcDNA5/FRT plasmids were generated as illustrated in FIGS. 1A-1C. The plasmids encoded an antigenic peptide called P5R (Govern et al., *Proc. Natl. Acad. Sci. USA,* 107: 8724-8729, 2010) linked to I-A$^b$ beta chains with random nucleotide substitutions in the codons for the CD4 binding sites on the beta chain and flanked by flippase recognition target (FRT) sites (Mortensen, *Curr. Protoc. Mol. Biol.,* Chapter 23: Unit 23 21, 2006). The library was then introduced by transfection along with a plasmid encoding flippase into a CHO cell line containing the I-A$^b$ alpha chain and a single FRT target site in the genome. Individual CHO cells then recombined a single I-A$^b$ beta chain sequence into the target site. This strategy ensured that each CHO cell in the library displayed a single I-A$^b$ alpha/P5R:I-A$^b$ beta heterodimer (referred to as P5R:I-A$^b$) with a different combination of substitutions at the targeted four positions of the beta chain.

A mouse CD4/streptavidin-fluorochrome tetramer was also generated and used to select CD4 tetramer-binding CHO cells from the library. Small numbers of cells in the library bound the CD4 tetramer and these cells were serially enriched with several rounds of selection using magnetic beads coated with antibodies specific for the fluorochrome component of the CD4/streptavidin-fluorochrome tetramer (FIG. 2A). Single CD4 tetramer-binding cells were eventually sorted by flow cytometry. Two CHO clones called P5R:I-$A^b$-RI and P5R:I-$A^b$-RII, which bound stably to the CD4 tetramer were identified (FIG. 2B). These molecules had different substitutions at three of the four targeted amino acid positions in the I-$A^b$ beta chain. The I-$A^b$-RI beta chain had E137A, V142M, and L158W substitutions, while the I-$A^b$-RII beta chain had V142I, I148Y, and L158D substitutions (FIG. 4A).

Peptide-bound CD4 affinity-enhanced MHCII tetramers bind $CD4^+$ T cells with low affinity TCRs. P5R:I-$A^b$ wild-type, P5R:I-$A^b$-RI, and P5R:I-$A^b$-RII tetramer linked to streptavidin fluorochromes were generated. These reagents were tested for binding to B3K508 T cells, which express a transgene-encoded monoclonal TCR that binds to P5R:I-$A^b$ molecules with a low affinity (equilibrium dissociation constant ($K_D$) of 93 μM) (Govern et al. Proc. Natl. Acad. Sci. USA, 107: 8724-8729, 2010). A schematic illustrating the binding of the CD4 affinity-enhanced p:MHCII molecules is provided in FIG. 3. The conventional P5R:I-$A^b$ tetramer bound to B3K508 T cells at a level that was barely above background staining of the polyclonal B6 $CD4^+$ T cell population (FIG. 4B), which contain very few P5R:I-$A^b$-specific T cells. In contrast, the P5R:I-$A^b$-RI and P5R:I-$A^b$-RII tetramers bound to B3K508 T cells, nearly achieving baseline separation from the overall B6 population. Importantly, the P5R:I-$A^b$-RI and P5R:I-$A^b$-RII tetramers did not bind to the B6 T cell population appreciably better than the conventional tetramer, as shown by the dark gray histograms in the three plots in FIG. 4B. Thus, the P5R:I-$A^b$-RI and P5R:I-$A^b$-RII tetramers did not show enhanced binding to all $CD4^+$ T cells, only those with P5R:I-$A^b$-specific TCRs. Because both evolved tetramers produced similar binding profiles, they were used interchangeably in the following the experiments.

Figures 5B, 5C, 5D:
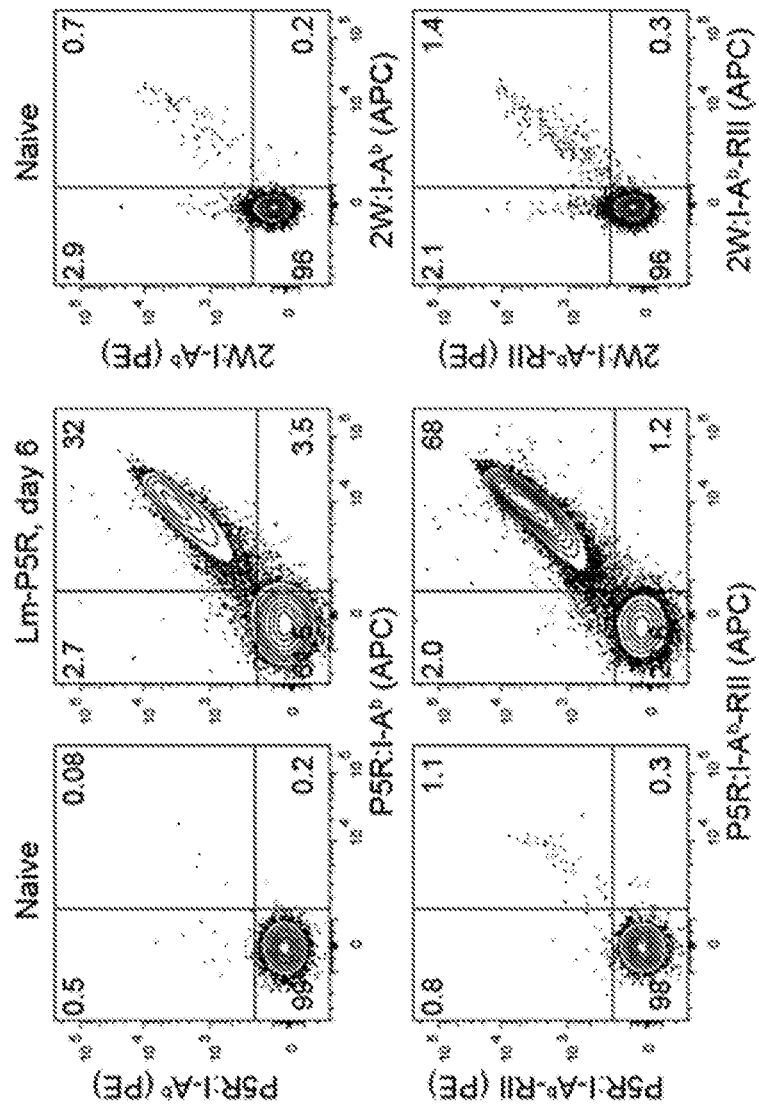

Foreign peptide-bound CD4 affinity-enhanced MHCII tetramers detect more $CD4^+$ T cells in polyclonal repertoires than conventional tetramers. The capacity of CD4 affinity-enhanced MHCII tetramers to detect relevant $CD4^+$ T cells in the polyclonal repertoires of mice was then assessed. Lymph node and spleen cells from several unmanipulated B6 mice or B6 mice infected with an attenuated actA strain of Listeria monocytogenes (Lm) bacteria expressing the P5R peptide (Lm-P5R) (Tubo et al., Cell, 153: 785-796, 2013) were stained with P5R:I-$A^b$ or P5R:I-$A^b$-RII tetramers labeled with allophycocyanin (APC) or phycoerythrin (PE), enriched with magnetic beads, and analyzed by flow cytometry. Cells were stained with the same tetramers conjugated with different fluorochromes to enhance the TCR specificity of the assay (Nelson et al., Immunity, 42: 95-107, 2015). Magnetic enrichment was necessary to detect the rare tetramer-binding cells (Moon et al. Immunity, 27: 203-213, 2007). About 20 naïve $CD4^+$ T cells were detected with the wild-type P5R:I-$A^b$ tetramer in each un-manipulated mouse (FIGS. 5A and 5B). In contrast, 240 naïve $CD4^+$ T cells were detected with the P5R:I-$A^b$-RII tetramer. Similarly, about 30,000 effector cells were detected with the conventional P5R:I-$A^b$ tetramer in Lm-P5R-infected mice, while the P5R:I-$A^b$-RII tetramer detected 80,000 effector cells (FIGS. 5A and 5C). These results demonstrate that the P5R:I-$A^b$-RII tetramer detects more naïve and effector $CD4^+$ T cells in the polyclonal repertoire than the conventional tetramer. The experiments with the B3K508 cells (FIG. 4B) suggest that the additional cells detected with the P5R:I-$A^b$-RII tetramer had low affinity TCRs.

Figure 6A:
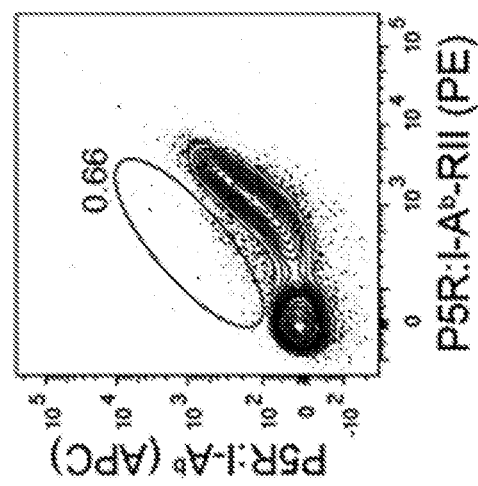
FIGS. 6A-6B are flow cytometry contour plots showing binding of P5R:I-A$^b$ tetramer or P5R:I-A$^b$-RII tetramer to cognate CD4+ T cells.
Figure 6B:
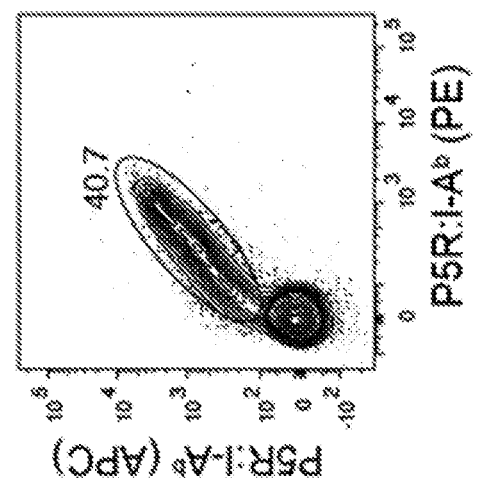

A competition experiment was carried out as another way to determine whether the P5R:I-$A^b$-RII tetramer binds to epitope-specific TCRs on $CD4^+$ T cells better than the conventional reagent. Spleen and lymph node cells from day seven Lm-P5R-infected mice were stained with a mixture of P5R:I-$A^b$ tetramer linked to APC and P5R:I-$A^b$ tetramer or P5R:I-$A^b$-RII tetramer linked to PE. The $CD4^+$ T cells in the sample stained with P5R:I-$A^b$ tetramer linked with the two different fluorochromes showed a diagonal pattern on a plot of APC versus PE staining intensity (FIG. 6A), consistent with individual cells having half their TCRs bound to one version of the P5R:I-$A^b$ tetramer and half with the other. In contrast, in the sample stained simultaneously with P5R:I-$A^b$-RII and P5R:I-$A^b$ tetramer, all tetramer-binding cells bound more P5R:I-$A^b$-RII than P5R:I-$A^b$ tetramer (FIG. 6B) and a sizeable fraction of the population, presumably composed of cells with the lowest affinity TCRs, bound to the P5R:I-$A^b$-RII but not the P5R:I-$A^b$ tetramer. The fact that the TCRs on all P5R:I-$A^b$ specific T cells bound to the P5R:I-$A^b$-RII tetramer better than the P5R:I-$A^b$ tetramer is strong evidence that the P5R:I-$A^b$-RII tetramer is a superior reagent than the conventional P5R:I-$A^b$ tetramer.

An I-$A^b$-RII tetramer containing a different foreign (non-mouse) antigenic peptide called 2W (Rees et al., Proc. Natl. Acad. Sci. USA, 96: 9781-9786, 1999) was produced to determine whether the I-$A^b$-RII molecule would confer enhanced binding to a Th population specific for an epitope other than P5R:I-$A^b$. The population of naïve $CD4^+$ T cells detected in B6 mice with the conventional 2W:I-$A^b$ tetramer amounts to about 300 cells (Moon et al., Immunity, 27: 203-213, 2007) and is thus much larger than the population of 20 cells detected with P5R:I-$A^b$ tetramer (FIGS. 5A and 5D). However, the 2W:I-$A^b$-RII tetramer detected an even larger population of 1,500 cells. This result indicates that the capacity of I-$A^b$-RII tetramers to detect more $CD4^+$ T cells in the polyclonal repertoire than conventional I-$A^b$ tetramers will be generalizable to other p:I-$A^b$-bound peptides.

An I-$A^b$-RII tetramer containing a mouse peptide called MOG peptide was produced to determine whether the I-$A^b$-RII molecule would confer enhanced binding to a Th population specific for a self-epitope. The MOG peptide:I-$A^b$-RII tetramer detected 42-fold more MOG peptide:I-$A^b$-specific $CD4^+$ T cells than the conventional MOG peptide:I-$A^b$ tetramer in unimmunized B6 mice and 4.2 times more in B6 mice immunized seven days earlier with the MOG peptide emulsified in complete Freund's adjuvant. This capacity of an I-$A^b$-RII tetramer to detect more self-epitope-specific $CD4^+$ T cells in the polyclonal repertoire than conventional I-$A^b$ tetramers could be a boon to autoimmunity research.

TABLE 1

Tetramer-Binding Cells in B6 Mice

| Tetramer | Unimmunized (mean ± sem) | MOG peptide-immunized (mean ± sem) |
| --- | --- | --- |
| MOG peptide:I-$A^b$ | 40 ± 14 | 1,244 ± 218 |
| MOG peptide:I-$A^b$-RII | 1,673 ± 125 | 5,191 ± 69 |

Improved capacity of CD4 affinity enhanced I-$A^b$ molecules to detect cognate T cells depends on CD4 molecules. The 2W:I-$A^b$ system and $Cd4^{-/-}$ mice (Locksley et al., Science, 261: 1448-1451, 1993) were used to determine whether the improved binding of CD4 affinity-enhanced I-$A^b$ molecules to cognate T cells depends on CD4. $Cd4^{-/-}$ B6 mice lack CD4 molecules but still contain a small population of I-$A^b$-restricted T cells (Locksley et al., supra, 1993). The conventional 2W:I-$A^b$ tetramer detected a small population of naïve T cells in unmanipulated CD4-deficient mice (FIG. 7A) and these cells proliferated to produce effector T cells six days after immunization with 2W peptide emulsified in complete Freund's adjuvant (FIG. 7B). Notably, the 2W:I-A$^b$-II tetramer detected the same number of naïve T cells in unmanipulated CD4-deficient mice (FIG. 7C) and effector cells in CD4-deficient mice immunized with 2W peptide in complete Freund's adjuvant (FIG. 7D) as the conventional 2W:I-A$^b$ tetramer. These results demonstrate that the improved capacity of CD4 affinity-enhanced I-A$^b$ molecules to detect cognate T cells depends on the T cell's expression of CD4 molecules.

Figure 8:
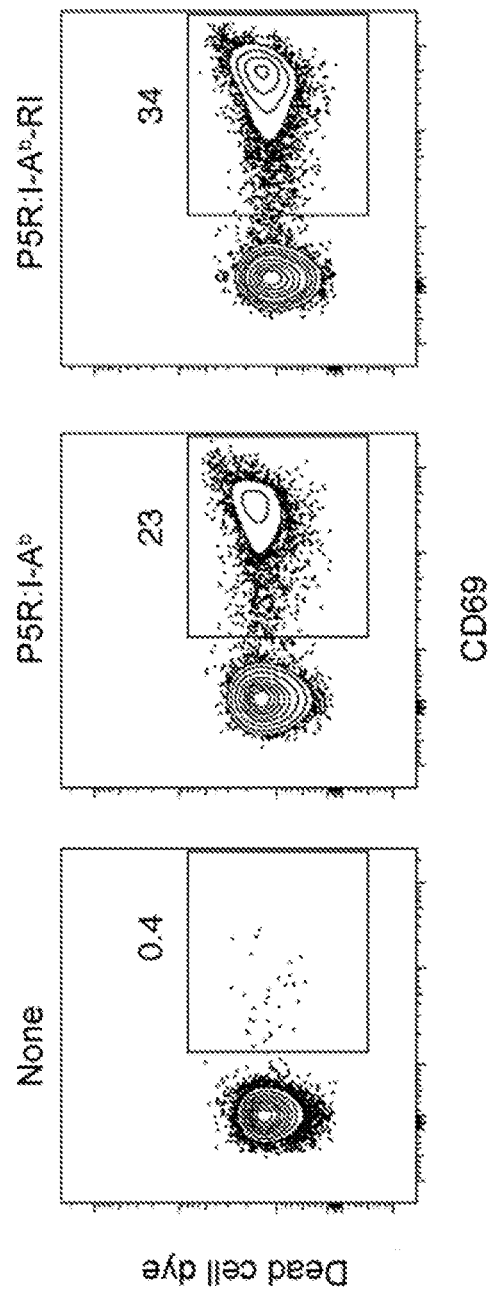
FIG. 8 shows flow cytometry plots showing CD69 expression by purified B3K508 cells cultured overnight with no stimulus or plate-bound P5R:I-A$^b$ or P5R:I-A$^b$-RI molecules.

Peptide-bound CD4 affinity-enhanced MHCII molecules activate CD4$^+$ T cells more efficiently than conventional molecules. It was also of interest to determine whether CD4 affinity-enhanced MHCII molecules activate CD4$^+$ T cells more effectively than wild-type molecules. Purified naïve B3K508 T cells were cultured overnight in tissue culture plates coated with streptavidin, streptavidin and P5R:I-A$^b$ molecules, or streptavidin and P5R:I-A$^b$-RI molecules. Some of the B3K508 T cells cultured in plates coated with P5R:I-A$^b$ molecules expressed CD69, a marker of TCR signaling (Cibrian et al., *Eur. J. Immunol.*, 47: 946-953, 2017), while B3K508 T cells cultured in plates coated with streptavidin alone did not (FIG. 8). More B3K508 T cells cultured in plates coated with P5R:I-A$^b$-RI molecules expressed CD69 than B3K508 T cells cultured in plates coated with wild-type P5R:I-A$^b$ molecules (FIG. 8). Thus, a peptide-bound CD4 affinity-enhanced MHCII molecule activates cognate CD4$^+$ T cells more efficiently than the comparable wild-type molecule.

EXEMPLARY SEQUENCES

```
>WT_I-A (b)_beta
                                         SEQ ID NO: 1
WFRNGQEETVGVSSTQLIRNGDWTFQVLVMLEMT >library_I-A_beta
                                         SEQ ID NO: 2
WFRNGQXETVGXSSTQLXRNGDWTFQVXVMLEMT >library_I-A_beta
                                         SEQ ID NO: 3
TGGTTCCGGAATGGCCAGNNNGAGACGGTGGGGNNNTCATCCACACAGC
TTNNNAGGAATGGGACTGGACCTTCCAGGTCNNNGTCATGCTGGACATG
ACC >WT = I-A (b/f/k)_beta
                                         SEQ ID NO: 4
WFRNGQEETVGVSSTQLIRNGDWTFQVLVM >RI
                                         SEQ ID NO: 5
WFRNGQAETVGMSSTQLIRNGDWTFQVWVM >RII
                                         SEQ ID NO: 6
WFRNGQEETVGISSTQLYRNGDWTFQVDVM >I-E (f/k)_beta
                                         SEQ ID NO: 7
WERNGKEEKT GIVSTGLVRN GDWTFQTLVM >I-A/E_beta consensus
                                         SEQ ID NO: 8
WFRNGXXEXX GXXSTXLXRN GDWTFQXXVM >I-A (b)_beta mature
                                         SEQ ID NO: 9
DSERHFVYQFMGECYFTNGTQRIRYVTRYIYNREEYVRYDSDVGEHRAV
TELGRPDAEYWNSQPEILERTRAELDTVCRHNYEGPETHTSLRRLEQPN
VVISLSRTEALNHHNTLVCSVTDFYPAKIKVRWFRNGQEETVGVSSTQL
IRNGDWTFQVLVMLEMTPRRGEVYTCHVEHPSLKSPITVEWRAQSESAW
SKMLSGIGGCVLGVIFLGLGLFIRHRSQKGPRGPPPAGLLQ >GeneBlockA
                                         SEQ ID NO: 10
GTTTAAACTTAAGCTTATGGCTCTGCAGATCCCCAGCCTCCTCCTCTCA
GCTGCTGTGGTGGTGCTGATGGTGCTGAGCAGCCCCGGGACTGAGGGCG
GAGATTCCGAGGCCCAGAAGGCCCGCGCCAACAAGGCCGTGGACAAGGC
CGGCGGCGGAGGTACTAGTGGCGGTGGAAGTGGAGGGTCTGAAAGGCAT
TTCGTGTACCAGTTCATGGGCGAGTGCTACTTCACCAACGGGACGCAGC
GCATACGATATGTGACCAGATACATCTACAACCGGGAGGAGTACGTGCG
CTACGACAGCGACGTGGGCGAGCACCGCGCGGTGACCGAGCTGGGCGG
CCAGACGCCGAGTACTGGAACAGCCAGCCGGAGATCCTGGAGCGAACGC
GGGCCGAGCTGGACACGGTGTGCAGACACAACTACGAGGGGCCGGAGAC
CCACACCTCCCTGCGGCGGCTTGAACAGCCCAATGTCGTCATCTCCCTG
TCCAGGACAGAGGCCCTCAACCACCACAACACTCTGGTCTGCTCAGTGA
CAGATTTCTACCCAGCCAAGATCAAAGTGCGCTGGTTCCGGAATGGCCA
GATGCATGTCATGCTGGAGATGACCCCTCGGCGGGAGAGGTCTACACC
TGTCACGTGGAGCATCCCAGCCTGAAGAGCCCCATCACTGTGGAGTGGA
GGGCACAGTCTGAGTCTGCCTGGAGCAAGATGTTGAGCGGCATCGGGGG
CTGCGTGCTTGGGGTGATCTTCCTCGGGCTTGGCCTTTTCATCCGTCAC
AGGAGTCAGAAAGGACCTCGAGGCCCTCCTCCAGCAGGGCTCCTGCAGT
GAAGCTTGGTACCGAGC >Forward
                                         SEQ ID NO: 11
5'-GTCATGCTGGAGATGACCCCTCGG-3'

>Reverse
                                         SEQ ID NO: 12
5'-CTGGCCATTCCGGAACCAGCG-3'

>Reverse
                                         SEQ ID NO: 13
5'-GTCATCTCCAGCATGAC-3'

>ForwardCD4
                                         SEQ ID NO: 14
5'-CCCCCGAATTCATGTGCCGAGCCATCTCTCTTA-3'

>ReverseCD4
                                         SEQ ID NO: 15
CCCCCGTCGACTTAATGATGATGATGATGATGTTCATGCCATTCAATTT
TCTGCGCTTCAAAAATATCGTTCAGGCCGCTGCCGCCGCTGCCGCCTGT
CTGGTTCACCCCTCTGGAT >I-A (b)_beta monomer
                                         SEQ ID NO: 16
MALQIPSLLLSAAVVVLMVLSSPGTEGEAQKARANKAVDKAGGGGTSGG
GSGGGSERHFVYQFMGECYFTNGTQRIRYVTRYIYNREEYVRYDSDVGEH
RAVTELGRPDAEYWNSQPEILERTRAELDTVCRHNYEGPETHTSLRRLE
QPNVVISLSRTEALNHHNTLVCSVTDFYPAKIKVRWFRNGQEETVGVSS
TQLIRNGDWTFQVLVMLEMTPRRGEVYTCHVEHPSLKSPITVEWRAQSE
SAWSKGGGGSTTAPSAQLKKKLQALKKKNAQLKWKLQALKKKLAQHHHH
HH >I-A (b)_alpha monomer
                                         SEQ ID NO: 17
MPCSRALILGVLALTTMLSLCGGEDDIEADHVGTYGISVYQSPGDIGQY
TFEFDGDELFYVDLDKKETVWMLPEFGQLASFDPQGGLQNIAVVKHNLG
VLTKRSNSTPATNEAPQATVFPKSPVLLGQPNTLICFVDNIFPPVINIT
WLRNSKSVADGVYETSFFVNRDYSPHKLSYLTFIPSDDDIYDCKVEHWG
LEEPVLKHWEPEIPAPMSELTETGGGGSTTAPSAQLEKELQALEKENAQ
LEWELQALEKELAQGGSGGSGLNDIFEAQKIEWHE >I-A (b)_beta signal
                                         SEQ ID NO: 18
MALQIPSLLLSAAVVVLMVLSSPGTEG >P5R peptide
                                         SEQ ID NO: 19
EAQKARANKAVDKA >linker
                                         SEQ ID NO: 20
GGGGTSGGGSGGS
```

>I-A (b)_beta extracellular minus two

SEQ ID NO: 21

ERHFVYQFMGECYFTNGTQRIRYVTRYIYNREEYVRYDSDVGEHRAVTE
LGRPDAEYWNSQPEILERTRAELDTVCRHNYEGPETHTSLRRLEQPNVV
ISLSRTEALNHHNTLVCSVTDFYPAKIKVRWFRNGQEETVGVSSTQLIR
NGDWTFQVLVMLEMTPRRGEVYTCHVEHPSLKSPITVEWRAQSESAWSK

>GGGGS

SEQ ID NO: 22

>basic leucine zipper

SEQ ID NO: 23

TTAPSAQLKKKLQALKKKNAQLKWKLQALKKKLAQ

>HisTag

SEQ ID NO: 24

HHHHHH

>I-A (b)_alpha signal

SEQ ID NO: 25

MPCSRALILGVLALTTMLSLCGG

>I-A (b)_alpha extracellular

SEQ ID NO: 26

EDDIEADHVGTYGISVYQSPGDIGQYTFEFDGDELFYVDLDKKETVWML
PEFGQLASFDPQGGLQNIAVVKHNLGVLTKRSNSTPATNEAPQATVFPK
SPVLLGQPNTLICFVDNIFPPVINITWLRNSKSVADGVYETSFFVNRDY
SFHKLSYLTFIPSDDDIYDCKVEHWGLEEPVLKHWEPEIPAPMSELTET

>acidic leucine zipper

SEQ ID NO: 27

TTAPSAQLEKELQALEKENAQLEWELQALEKELAQ

>linker

SEQ ID NO: 28

GGSGGS

>BirA biotinylation signal sequence

SEQ ID NO: 29

GLNDIFEAQKIEWHE

>2W peptide

SEQ ID NO: 30

EAWGALANWAVDSA

>linker

SEQ ID NO: 31

GCGGTSGGGSGGS

>MOG peptide

SEQ ID NO: 32

GWYRSPFSRVV

SEQUENCE LISTING

```
<160> NUMBER OF SEQ ID NOS: 32

<210> SEQ ID NO 1
<211> LENGTH: 34
<212> TYPE: PRT
<213> ORGANISM: Artificial Sequence
<220> FEATURE:
<223> OTHER INFORMATION: Synthetic Construct

<400> SEQUENCE: 1

Trp Phe Arg Asn Gly Gln Glu Glu Thr Val Gly Val Ser Ser Thr Gln
1               5                   10                  15

Leu Ile Arg Asn Gly Asp Trp Thr Phe Gln Val Leu Val Met Leu Glu
            20                  25                  30

Met Thr

<210> SEQ ID NO 2
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7, 12, 18, 28
<223> OTHER INFORMATION: Xaa = any one of the 20 standard amino acid
      residues

<400> SEQUENCE: 2

Trp Phe Arg Asn Gly Gln Xaa Glu Thr Val Gly Xaa Ser Ser Thr Gln
1               5                   10                  15

Leu Xaa Arg Asn Gly Asp Trp Thr Phe Gln Val Xaa Val Met Leu Glu
            20                  25                  30

Met Thr

<210> SEQ ID NO 3
<211> LENGTH: 101
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20, 21, 34, 35, 36, 52, 53, 54, 81, 82, 83
<223> OTHER INFORMATION: n = A,T,C or G

<400> SEQUENCE: 3
tggttccgga atggccagnn ngagacggtg gggnnntcat ccacacagct tnnnaggaat      60
gggactggac cttccaggtc nnngtcatgc tggacatgac c                        101

<210> SEQ ID NO 4
<211> LENGTH: 30
<212> TYPE: PRT
<213> ORGANISM: Artificial Sequence
<220> FEATURE:
<223> OTHER INFORMATION: Synthetic Construct

<400> SEQUENCE: 4

Trp Phe Arg Asn Gly Gln Glu Glu Thr Val Gly Val Ser Ser Thr Gln
1               5                   10                  15

Leu Ile Arg Asn Gly Asp Trp Thr Phe Gln Val Leu Val Met
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic Construct

<400> SEQUENCE: 5

Trp Phe Arg Asn Gly Gln Ala Glu Thr Val Gly Met Ser Ser Thr Gln
1               5                   10                  15

Leu Ile Arg Asn Gly Asp Trp Thr Phe Gln Val Trp Val Met
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic Construct

<400> SEQUENCE: 6

Trp Phe Arg Asn Gly Gln Glu Glu Thr Val Gly Ile Ser Ser Thr Gln
1               5                   10                  15

Leu Tyr Arg Asn Gly Asp Trp Thr Phe Gln Val Asp Val Met
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic Construct

<400> SEQUENCE: 7

Trp Phe Arg Asn Gly Lys Glu Glu Lys Thr Gly Ile Val Ser Thr Gly
1               5                   10                  15

Leu Val Arg Asn Gly Asp Trp Thr Phe Gln Thr Leu Val Met
            20                  25                  30
```

-continued

<210> SEQ ID NO 8
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Gln or Lys
<220> FEATURE:
<221> NAME/KEY: VARIANT
<222> LOCATION: 7
<223> OTHER INFORMATION: Xaa = Glu or Ala
<220> FEATURE:
<221> NAME/KEY: VARIANT
<222> LOCATION: 9
<223> OTHER INFORMATION: Xaa = Thr or Lys
<220> FEATURE:
<221> NAME/KEY: VARIANT
<222> LOCATION: 10
<223> OTHER INFORMATION: Xaa = Val or Thr
<220> FEATURE:
<221> NAME/KEY: VARIANT
<222> LOCATION: 12
<223> OTHER INFORMATION: Xaa = Val or Ile or Met
<220> FEATURE:
<221> NAME/KEY: VARIANT
<222> LOCATION: 13
<223> OTHER INFORMATION: Xaa = Ser or Val
<220> FEATURE:
<221> NAME/KEY: VARIANT
<222> LOCATION: 16
<223> OTHER INFORMATION: Xaa = Gln or Gly
<220> FEATURE:
<221> NAME/KEY: VARIANT
<222> LOCATION: 18
<223> OTHER INFORMATION: Xaa = Ile or Val or Tyr
<220> FEATURE:
<221> NAME/KEY: VARIANT
<222> LOCATION: 27
<223> OTHER INFORMATION: Xaa = Val or Thr
<220> FEATURE:
<221> NAME/KEY: VARIANT
<222> LOCATION: 28
<223> OTHER INFORMATION: Xaa = Leu or Trp or Asp

<400> SEQUENCE: 8

```
Trp Phe Arg Asn Gly Xaa Xaa Glu Xaa Xaa Gly Xaa Xaa Ser Thr Xaa
1               5                   10                  15

Leu Xaa Arg Asn Gly Asp Trp Thr Phe Gln Xaa Xaa Val Met
            20                  25                  30
```

<210> SEQ ID NO 9
<211> LENGTH: 237
<212> TYPE: PRT
<213> ORGANISM: Artificial Sequence
<220> FEATURE:
<223> OTHER INFORMATION: Synthetic Construct

<400> SEQUENCE: 9

```
Asp Ser Glu Arg His Phe Val Tyr Gln Phe Met Gly Glu Cys Tyr Phe
1               5                   10                  15

Thr Asn Gly Thr Gln Arg Ile Arg Tyr Val Thr Arg Tyr Ile Tyr Asn
            20                  25                  30

Arg Glu Glu Tyr Val Arg Tyr Asp Ser Asp Val Gly Glu His Arg Ala
        35                  40                  45

Val Thr Glu Leu Gly Arg Pro Asp Ala Glu Tyr Trp Asn Ser Gln Pro
    50                  55                  60

Glu Ile Leu Glu Arg Thr Arg Ala Glu Leu Asp Thr Val Cys Arg His
65                  70                  75                  80

```
Asn Tyr Glu Gly Pro Glu Thr His Thr Ser Leu Arg Arg Leu Glu Gln
                85                  90                  95
Pro Asn Val Val Ile Ser Leu Ser Arg Thr Glu Ala Leu Asn His His
            100                 105                 110
Asn Thr Leu Val Cys Ser Val Thr Asp Phe Tyr Pro Ala Lys Ile Lys
        115                 120                 125
Val Arg Trp Phe Arg Asn Gly Gln Glu Glu Thr Val Gly Val Ser Ser
    130                 135                 140
Thr Gln Leu Ile Arg Asn Gly Asp Trp Thr Phe Gln Val Leu Val Met
145                 150                 155                 160
Leu Glu Met Thr Pro Arg Arg Gly Glu Val Tyr Thr Cys His Val Glu
                165                 170                 175
His Pro Ser Leu Lys Ser Pro Ile Thr Val Glu Trp Arg Ala Gln Ser
            180                 185                 190
Glu Ser Ala Trp Ser Lys Met Leu Ser Gly Ile Gly Gly Cys Val Leu
        195                 200                 205
Gly Val Ile Phe Leu Gly Leu Gly Leu Phe Ile Arg His Arg Ser Gln
    210                 215                 220
Lys Gly Pro Arg Gly Pro Pro Ala Gly Leu Leu Gln
225                 230                 235

<210> SEQ ID NO 10
<211> LENGTH: 850
<212> TYPE: DNA
<213> ORGANISM: Artificial Sequence
<220> FEATURE:
<223> OTHER INFORMATION: Synthetic Construct

<400> SEQUENCE: 10
gtttaaactt aagcttatgg ctctgcagat ccccagcctc ctcctctcag ctgctgtggt      60
ggtgctgatg gtgctgagca gccccgggac tgagggcgga gattccgagg cccagaaggc     120
ccgcgccaac aaggccgtgg acaaggccgg cggcggaggt actagtggcg gtggaagtgg     180
agggtctgaa aggcatttcg tgtaccagtt catgggcgag tgctacttca ccaacgggac     240
gcagcgcata cgatatgtga ccagatacat ctacaaccgg gaggagtacg tgcgctacga     300
cagcgacgtg ggcgagcacc gcgcggtgac cgagctgggg cggccagacg ccgagtactg     360
gaacagccag ccggagatcc tggagcgaac gcgggccgga ctggacacgg tgtgcagaca     420
caactacgag gggccggaga cccacacctc cctgcggcgg cttaacagcc caatgtcgt      480
catctccctg tccaggacag aggccctcaa ccaccacaac actctggtct gctcagtgac     540
agatttctac ccagccaaga tcaaagtgcg ctggttccgg aatggccaga tgcatgtcat     600
gctggagatg acccctcggc ggggagaggt ctacacctgt cacgtggagc atcccagcct     660
gaagagcccc atcactgtgg agtggagggc acagtctgag tctgcctgga gcaagatgtt     720
gagcggcatc gggggctgcg tgcttggggt gatcttcctc gggcttggcc ttttcatccg     780
tcacaggagt cagaaaggac ctcgaggccc tcctccagca gggctcctgc agtgaagctt     840
ggtaccgagc                                                            850

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct
```

<400> SEQUENCE: 11
gtcatgctgg agatgacccc tcgg                                              24

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
ctggccattc cggaaccagc g                                                 21

<210> SEQ ID NO 13
<211> LENGTH: 17
<212> TYPE: DNA
<213> ORGANISM: Artificial Sequence
<220> FEATURE:
<223> OTHER INFORMATION: Synthetic Construct

<400> SEQUENCE: 13
gtcatctcca gcatgac                                                      17

<210> SEQ ID NO 14
<211> LENGTH: 33
<212> TYPE: DNA
<213> ORGANISM: Artificial Sequence
<220> FEATURE:
<223> OTHER INFORMATION: Synthetic Construct

<400> SEQUENCE: 14
cccccgaatt catgtgccga gccatctctc tta                                    33

<210> SEQ ID NO 15
<211> LENGTH: 117
<212> TYPE: DNA
<213> ORGANISM: Artificial Sequence
<220> FEATURE:
<223> OTHER INFORMATION: Synthetic Construct

<400> SEQUENCE: 15
cccccgtcga cttaatgatg atgatgatga tgttcatgcc attcaatttt ctgcgcttca       60
aaaatatcgt tcaggccgct gccgccgctg ccgcctgtct ggttcacccc tctggat         117

<210> SEQ ID NO 16
<211> LENGTH: 296
<212> TYPE: PRT
<213> ORGANISM: Artificial Sequence
<220> FEATURE:
<223> OTHER INFORMATION: Synthetic Construct

<400> SEQUENCE: 16

Met Ala Leu Gln Ile Pro Ser Leu Leu Leu Ser Ala Ala Val Val Val
1               5                   10                  15

Leu Met Val Leu Ser Ser Pro Gly Thr Glu Gly Glu Ala Gln Lys Ala
                20                  25                  30

Arg Ala Asn Lys Ala Val Asp Lys Ala Gly Gly Gly Gly Thr Ser Gly
            35                  40                  45

Gly Gly Ser Gly Gly Ser Glu Arg His Phe Val Tyr Gln Phe Met Gly
        50                  55                  60

Glu Cys Tyr Phe Thr Asn Gly Thr Gln Arg Ile Arg Tyr Val Thr Arg
65                  70                  75                  80

```
Tyr Ile Tyr Asn Arg Glu Glu Tyr Val Arg Tyr Asp Ser Asp Val Gly
                85                  90                  95

Glu His Arg Ala Val Thr Glu Leu Gly Arg Pro Asp Ala Glu Tyr Trp
            100                 105                 110

Asn Ser Gln Pro Glu Ile Leu Glu Arg Thr Arg Ala Glu Leu Asp Thr
        115                 120                 125

Val Cys Arg His Asn Tyr Glu Gly Pro Glu Thr His Thr Ser Leu Arg
    130                 135                 140

Arg Leu Glu Gln Pro Asn Val Val Ile Ser Leu Ser Arg Thr Glu Ala
145                 150                 155                 160

Leu Asn His His Asn Thr Leu Val Cys Ser Val Thr Asp Phe Tyr Pro
                165                 170                 175

Ala Lys Ile Lys Val Arg Trp Phe Arg Asn Gly Gln Glu Glu Thr Val
            180                 185                 190

Gly Val Ser Ser Thr Gln Leu Ile Arg Asn Gly Asp Trp Thr Phe Gln
        195                 200                 205

Val Leu Val Met Leu Glu Met Thr Pro Arg Arg Gly Glu Val Tyr Thr
    210                 215                 220

Cys His Val Glu His Pro Ser Leu Lys Ser Pro Ile Thr Val Glu Trp
225                 230                 235                 240

Arg Ala Gln Ser Glu Ser Ala Trp Ser Lys Gly Gly Gly Ser Thr
                245                 250                 255

Thr Ala Pro Ser Ala Gln Leu Lys Lys Leu Gln Ala Leu Lys Lys
                260                 265                 270

Lys Asn Ala Gln Leu Lys Trp Lys Leu Gln Ala Leu Lys Lys Lys Leu
            275                 280                 285

Ala Gln His His His His His His
        290                 295

<210> SEQ ID NO 17
<211> LENGTH: 280
<212> TYPE: PRT
<213> ORGANISM: Artificial Sequence
<220> FEATURE:
<223> OTHER INFORMATION: Synthetic Construct

<400> SEQUENCE: 17

Met Pro Cys Ser Arg Ala Leu Ile Leu Gly Val Leu Ala Leu Thr Thr
1               5                   10                  15

Met Leu Ser Leu Cys Gly Gly Glu Asp Asp Ile Glu Ala Asp His Val
            20                  25                  30

Gly Thr Tyr Gly Ile Ser Val Tyr Gln Ser Pro Gly Asp Ile Gly Gln
        35                  40                  45

Tyr Thr Phe Glu Phe Asp Gly Asp Glu Leu Phe Tyr Val Asp Leu Asp
    50                  55                  60

Lys Lys Glu Thr Val Trp Met Leu Pro Glu Phe Gly Gln Leu Ala Ser
65                  70                  75                  80

Phe Asp Pro Gln Gly Gly Leu Gln Asn Ile Ala Val Val Lys His Asn
                85                  90                  95

Leu Gly Val Leu Thr Lys Arg Ser Asn Ser Thr Pro Ala Thr Asn Glu
            100                 105                 110

Ala Pro Gln Ala Thr Val Phe Pro Lys Ser Pro Val Leu Leu Gly Gln
        115                 120                 125

Pro Asn Thr Leu Ile Cys Phe Val Asp Asn Ile Phe Pro Pro Val Ile
    130                 135                 140
```

```
Asn Ile Thr Trp Leu Arg Asn Ser Lys Ser Val Ala Asp Gly Val Tyr
145                 150                 155                 160

Glu Thr Ser Phe Phe Val Asn Arg Asp Tyr Ser Phe His Lys Leu Ser
                165                 170                 175

Tyr Leu Thr Phe Ile Pro Ser Asp Asp Ile Tyr Asp Cys Lys Val
            180                 185                 190

Glu His Trp Gly Leu Glu Pro Val Leu Lys His Trp Glu Pro Glu
            195                 200                 205

Ile Pro Ala Pro Met Ser Glu Leu Thr Glu Thr Gly Gly Gly Ser
        210                 215                 220

Thr Thr Ala Pro Ser Ala Gln Leu Glu Lys Glu Leu Gln Ala Leu Glu
225                 230                 235                 240

Lys Glu Asn Ala Gln Leu Glu Trp Glu Leu Gln Ala Leu Glu Lys Glu
                245                 250                 255

Leu Ala Gln Gly Gly Ser Gly Gly Ser Gly Leu Asn Asp Ile Phe Glu
                260                 265                 270

Ala Gln Lys Ile Glu Trp His Glu
            275                 280
```

<210> SEQ ID NO 18
<211> LENGTH: 27
<212> TYPE: PRT
<213> ORGANISM: Artificial Sequence
<220> FEATURE:
<223> OTHER INFORMATION: Synthetic Construct

<400> SEQUENCE: 18

```
Met Ala Leu Gln Ile Pro Ser Leu Leu Leu Ser Ala Ala Val Val Val
1               5                   10                  15

Leu Met Val Leu Ser Ser Pro Gly Thr Glu Gly
            20                  25
```

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

```
Glu Ala Gln Lys Ala Arg Ala Asn Lys Ala Val Asp Lys Ala
1               5                   10
```

<210> SEQ ID NO 20
<211> LENGTH: 13
<212> TYPE: PRT
<213> ORGANISM: Artificial Sequence
<220> FEATURE:
<223> OTHER INFORMATION: Synthetic Construct

<400> SEQUENCE: 20

```
Gly Gly Gly Gly Thr Ser Gly Gly Ser Gly Gly Ser
1               5                   10
```

<210> SEQ ID NO 21
<211> LENGTH: 196
<212> TYPE: PRT
<213> ORGANISM: Artificial Sequence
<220> FEATURE:
<223> OTHER INFORMATION: Synthetic Construct

<400> SEQUENCE: 21

Glu Arg His Phe Val Tyr Gln Phe Met Gly Glu Cys Tyr Phe Thr Asn
1               5                   10                  15

Gly Thr Gln Arg Ile Arg Tyr Val Thr Arg Tyr Ile Tyr Asn Arg Glu
            20                  25                  30

Glu Tyr Val Arg Tyr Asp Ser Asp Val Gly Glu His Arg Ala Val Thr
                35                  40                  45

Glu Leu Gly Arg Pro Asp Ala Glu Tyr Trp Asn Ser Gln Pro Glu Ile
        50                  55                  60

Leu Glu Arg Thr Arg Ala Glu Leu Asp Thr Val Cys Arg His Asn Tyr
65                  70                  75                  80

Glu Gly Pro Glu Thr His Thr Ser Leu Arg Arg Leu Glu Gln Pro Asn
                85                  90                  95

Val Val Ile Ser Leu Ser Arg Thr Glu Ala Leu Asn His His Asn Thr
            100                 105                 110

Leu Val Cys Ser Val Thr Asp Phe Tyr Pro Ala Lys Ile Lys Val Arg
                115                 120                 125

Trp Phe Arg Asn Gly Gln Glu Thr Val Gly Val Ser Ser Thr Gln
        130                 135                 140

Leu Ile Arg Asn Gly Asp Trp Thr Phe Gln Val Leu Val Met Leu Glu
145                 150                 155                 160

Met Thr Pro Arg Arg Gly Glu Val Tyr Thr Cys His Val Glu His Pro
                165                 170                 175

Ser Leu Lys Ser Pro Ile Thr Val Glu Trp Arg Ala Gln Ser Glu Ser
            180                 185                 190

Ala Trp Ser Lys
        195

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Gly Gly Gly Gly Ser
1               5

<210> SEQ ID NO 23
<211> LENGTH: 35
<212> TYPE: PRT
<213> ORGANISM: Artificial Sequence
<220> FEATURE:
<223> OTHER INFORMATION: Synthetic Construct

<400> SEQUENCE: 23

Thr Thr Ala Pro Ser Ala Gln Leu Lys Lys Lys Leu Gln Ala Leu Lys
1               5                   10                  15

Lys Lys Asn Ala Gln Leu Lys Trp Lys Leu Gln Ala Leu Lys Lys Lys
            20                  25                  30

Leu Ala Gln
        35

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

His His His His His His
1               5

<210> SEQ ID NO 25
<211> LENGTH: 23
<212> TYPE: PRT
<213> ORGANISM: Artificial Sequence
<220> FEATURE:
<223> OTHER INFORMATION: Synthetic Construct

<400> SEQUENCE: 25

Met Pro Cys Ser Arg Ala Leu Ile Leu Gly Val Leu Ala Leu Thr Thr
1               5                   10                  15

Met Leu Ser Leu Cys Gly Gly
            20

<210> SEQ ID NO 26
<211> LENGTH: 196
<212> TYPE: PRT
<213> ORGANISM: Artificial Sequence
<220> FEATURE:
<223> OTHER INFORMATION: Synthetic Construct

<400> SEQUENCE: 26

Glu Asp Asp Ile Glu Ala Asp His Val Gly Thr Tyr Gly Ile Ser Val
1               5                   10                  15

Tyr Gln Ser Pro Gly Asp Ile Gly Gln Tyr Thr Phe Glu Phe Asp Gly
            20                  25                  30

Asp Glu Leu Phe Tyr Val Asp Leu Asp Lys Lys Glu Thr Val Trp Met
        35                  40                  45

Leu Pro Glu Phe Gly Gln Leu Ala Ser Phe Asp Pro Gln Gly Gly Leu
    50                  55                  60

Gln Asn Ile Ala Val Val Lys His Asn Leu Gly Val Leu Thr Lys Arg
65                  70                  75                  80

Ser Asn Ser Thr Pro Ala Thr Asn Glu Ala Pro Gln Ala Thr Val Phe
                85                  90                  95

Pro Lys Ser Pro Val Leu Leu Gly Gln Pro Asn Thr Leu Ile Cys Phe
            100                 105                 110

Val Asp Asn Ile Phe Pro Pro Val Ile Asn Ile Thr Trp Leu Arg Asn
        115                 120                 125

Ser Lys Ser Val Ala Asp Gly Val Tyr Glu Thr Ser Phe Phe Val Asn
    130                 135                 140

Arg Asp Tyr Ser Phe His Lys Leu Ser Tyr Leu Thr Phe Ile Pro Ser
145                 150                 155                 160

Asp Asp Asp Ile Tyr Asp Cys Lys Val Glu His Trp Gly Leu Glu Glu
                165                 170                 175

Pro Val Leu Lys His Trp Glu Pro Glu Ile Pro Ala Pro Met Ser Glu
            180                 185                 190

Leu Thr Glu Thr
        195

<210> SEQ ID NO 27
<211> LENGTH: 35
<212> TYPE: PRT
<213> ORGANISM: Artificial Sequence
<220> FEATURE:
<223> OTHER INFORMATION: Synthetic Construct

<400> SEQUENCE: 27

-continued

```
Thr Thr Ala Pro Ser Ala Gln Leu Glu Lys Glu Leu Gln Ala Leu Glu
1               5                   10                  15

Lys Glu Asn Ala Gln Leu Glu Trp Glu Leu Gln Ala Leu Glu Lys Glu
            20                  25                  30

Leu Ala Gln
        35

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Gly Gly Ser Gly Gly Ser
1               5

<210> SEQ ID NO 29
<211> LENGTH: 15
<212> TYPE: PRT
<213> ORGANISM: Artificial Sequence
<220> FEATURE:
<223> OTHER INFORMATION: Synthetic Construct

<400> SEQUENCE: 29

Gly Leu Asn Asp Ile Phe Glu Ala Gln Lys Ile Glu Trp His Glu
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Glu Ala Trp Gly Ala Leu Ala Asn Trp Ala Val Asp Ser Ala
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic Construct

<400> SEQUENCE: 31

Gly Cys Gly Gly Thr Ser Gly Gly Ser Gly Gly Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Gly Trp Tyr Arg Ser Pro Phe Ser Arg Val Val
1               5                   10
```

We claim:

1. A variant major histocompatibility complex class II (MHCII) beta chain comprising an extracellular domain comprising an amino acid substitution in one or more positions, wherein the positions are numbered in correspondence with the amino acid sequence of a wild type MHCII beta chain of SEQ ID NO:9, and wherein the variant comprises the amino acid sequence of SEQ ID NO:8 with an amino acid substitution at position 158 which is L158W or L158D.

2. The variant MHCII beta chain of claim 1, further comprising an amino acid substitution at position 142, which is V142M or V142I.

3. The variant MHCII beta chain of claim 2, comprising V142M, and L158W, and further comprising E137A.

4. The variant MHCII beta chain of claim 3, comprising the amino acid sequence of SEQ ID NO:5.

5. The variant MHCII beta chain of claim 2, comprising V142I, I148Y, and L158D.

6. The variant MHCII beta chain of claim 5, comprising the amino acid sequence of SEQ ID NO:6.

7. The variant MHCII beta chain of claim 2, wherein the variant is a fusion protein further comprising a heterologous peptide of 10 to 25 amino acids in length and a glycine-rich linker of 10 to 15 amino acids in length at its amino-terminus.

8. A heterodimer comprising the variant MHCII beta chain of claim 7, and a MHCII alpha chain, and wherein the heterologous peptide is bound in a peptide-binding groove of the heterodimer.

9. A multimer comprising two, three or four heterodimers of claim 8.

10. The multimer of claim 9, wherein the multimer further comprising a fluorescent tag.

11. A nucleic acid encoding the variant MHCII beta chain of claim 1.

12. An expression cassette comprising the nucleic acid of claim 11 in operable combination with a promoter.

13. An expression vector comprising the expression cassette of claim 12 and an antibiotic resistance gene.

14. A host cell comprising the expression vector of claim 13.

15. A composition comprising a plurality of multimers of claim 10 and an isotonic solution.

16. A kit comprising the composition of claim 15, and instructions for use of the composition to assess binding of the multimers to CD4$^+$ T cells specific for the heterologous peptide.

17. A method for assessing CD4$^+$ T cell frequency, comprising contacting a sample comprising a plurality of CD4$^+$ T cells with the composition of claim 15 under conditions suitable for binding CD4$^+$ T cells specific for the heterologous peptide to the multimers.

18. The method of claim 17, wherein CD4$^+$ T cell frequency is assessed by flow cytometry immunofluorescence assay.

19. The method of claim 18, further comprising contacting the sample with a monoclonal antibody specific for a cell surface marker under conditions suitable for binding CD4$^+$ T cells expressing the surface marker.

20. An article of manufacture comprising a solid support to which a plurality of the heterodimers of claim 8 are affixed.

21. The article of manufacture of claim 20, wherein the solid support is tissue culture ware selected from the group consisting of a dish, a flask, and a multi-well plate.

22. A method for activating T cells, comprising incubating a sample comprising a plurality of T cells in culture medium in the tissue culture ware of claim 21 under conditions suitable for activating T cells specific for the heterologous peptide.

* * * * *